United States Patent
Kuduk et al.

(10) Patent No.: US 9,745,284 B2
(45) Date of Patent: Aug. 29, 2017

(54) 2-PYRIDYLOXY-4-ETHER OREXIN RECEPTOR ANTAGONISTS

(71) Applicant: MERCK SHARP & DOHME CORP., Rahway, NJ (US)

(72) Inventors: Scott D. Kuduk, Harleysville, PA (US); Jason W. Skudlarek, Audubon, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/772,272

(22) PCT Filed: Mar. 3, 2014

(86) PCT No.: PCT/US2014/019843
§ 371 (c)(1),
(2) Date: Sep. 2, 2015

(87) PCT Pub. No.: WO2014/137883
PCT Pub. Date: Sep. 12, 2014

(65) Prior Publication Data
US 2016/0016935 A1 Jan. 21, 2016

Related U.S. Application Data

(60) Provisional application No. 61/774,710, filed on Mar. 8, 2013.

(51) Int. Cl.
| | | |
|---|---|---|
| *C07D 401/14* | (2006.01) | |
| *C07D 405/14* | (2006.01) | |
| *C07D 413/14* | (2006.01) | |
| *C07D 401/12* | (2006.01) | |
| *C07D 409/14* | (2006.01) | |
| *C07D 417/14* | (2006.01) | |

(52) U.S. Cl.
CPC ......... *C07D 401/14* (2013.01); *C07D 401/12* (2013.01); *C07D 405/14* (2013.01); *C07D 409/14* (2013.01); *C07D 413/14* (2013.01); *C07D 417/14* (2013.01)

(58) Field of Classification Search
CPC .................................. C07D 401/14

USPC ........................................ 546/194; 514/318
See application file for complete search history.

(56) References Cited

U.S. PATENT DOCUMENTS

| | | | |
|---|---|---|---|
| 8,071,600 B2* | 12/2011 | Yamashita | C07D 333/54 514/252.11 |
| 8,129,380 B2* | 3/2012 | Menear | C07D 401/10 514/248 |
| 8,242,121 B2 | 8/2012 | Coleman et al. | |
| 8,569,311 B2 | 10/2013 | Breslin et al. | |
| 8,710,076 B2 | 4/2014 | Breslin et al. | |
| 2010/0168134 A1 | 7/2010 | Breslin et al. | |
| 2011/0201632 A1 | 8/2011 | Breslin et al. | |
| 2012/0149723 A1 | 6/2012 | Di Fabio | |
| 2012/0232052 A1 | 9/2012 | Yamagishi | |
| 2015/0252033 A1 | 9/2015 | Kuduk et al. | |
| 2015/0291558 A1 | 10/2015 | Kuduk et al. | |
| 2015/0322039 A1 | 11/2015 | Kuduk et al. | |
| 2015/0322040 A1 | 11/2015 | Kuduk et al. | |
| 2015/0322041 A1 | 11/2015 | Kuduk et al. | |

FOREIGN PATENT DOCUMENTS

| | | |
|---|---|---|
| WO | 2006113704 | * 10/2006 |
| WO | WO2014099696 | 6/2014 |
| WO | WO2014137883 | 9/2014 |
| WO | WO2014176142 | 10/2014 |
| WO | WO2014176144 | 10/2014 |
| WO | WO2014176146 | 10/2014 |
| WO | WO2015088864 | 6/2015 |
| WO | WO2015088865 | 6/2015 |
| WO | WO2015095108 | 6/2015 |
| WO | WO2015095442 | 6/2015 |

* cited by examiner

*Primary Examiner* — Patricial L Morris
(74) *Attorney, Agent, or Firm* — J. Eric Thies; John C. Todaro

(57) ABSTRACT

The present invention is directed to 2-pyridyloxy-4-ether compounds which are antagonists of orexin receptors. The present invention is also directed to uses of the 2-pyridyloxy-4-ether compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the prevention or treatment of such diseases in which orexin receptors are involved.

6 Claims, No Drawings

2-PYRIDYLOXY-4-ETHER OREXIN RECEPTOR ANTAGONISTS

CROSS REFERENCE TO RELATED APPLICATIONS

This application is a U.S. National Phase application under 35 U.S.C. §371 of PCT Application No. PCT/US2014/019843, filed Mar. 3, 2014, which claims priority under 35 U.S.C. §119(e) from U.S. Ser. No. 61/774,710, filed Mar. 8, 2013.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to 2-pyridyloxy-4-ether compounds which are antagonists of orexin receptors. The present invention is also directed to uses of the 2-pyridyloxy-4-ether compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the prevention or treatment of such diseases in which orexin receptors are involved.

DETAILED DESCRIPTION OF THE INVENTION

The present invention is directed to compounds of the formula I:

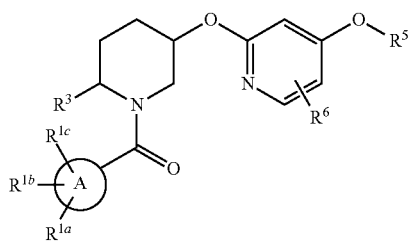

wherein:
A is selected from the group consisting of phenyl, naphthyl and heteroaryl;
$R^{1a}$, $R^{1b}$ and $R^{1c}$ are independently selected from the group consisting of:
  (1) hydrogen,
  (2) halogen,
  (3) hydroxyl,
  (4) —(C=O)$_m$—O$_n$—C$_{1-6}$ alkyl, where m is 0 or 1, n is 0 or 1 (wherein if m is 0 or n is 0, a bond is present) and where the alkyl is unsubstituted or substituted with one or more substituents selected from $R^4$,
  (5) —(C=O)$_m$—O$_n$—C$_{3-6}$ cycloalkyl, where the cycloalkyl is unsubstituted or substituted with one or more substituents selected from $R^4$,
  (6) —(C=O)$_m$—C$_{2-4}$ alkenyl, where the alkenyl is unsubstituted or substituted with one or more substituents selected from $R^4$,
  (7) —(C=O)$_m$—C$_{2-4}$ alkynyl, where the alkynyl is unsubstituted or substituted with one or more substituents selected from $R^4$,
  (8) —(C=O)$_m$—O$_n$-phenyl or —(C=O)$_m$—O$_n$-naphthyl, where the phenyl or naphthyl is unsubstituted or substituted with one or more substituents selected from $R^4$,
  (9) —(C=O)$_m$—O$_n$-heterocycle, where the heterocycle is unsubstituted or substituted with one or more substituents selected from $R^4$,
  (10) —(C=O)$_m$—NR$^{10}$R$^{11}$, wherein $R^{10}$ and $R^{11}$ are independently selected from the group consisting of:
    (a) hydrogen,
    (b) C$_{1-6}$ alkyl, which is unsubstituted or substituted with $R^4$,
    (c) C$_{3-6}$ alkenyl, which is unsubstituted or substituted with $R^4$,
    (d) C$_{3-6}$ alkynyl, which is unsubstituted or substituted with $R^4$,
    (e) C$_{3-6}$ cycloalkyl which is unsubstituted or substituted with $R^4$,
    (f) phenyl, which is unsubstituted or substituted with $R^4$, and
    (g) heterocycle, which is unsubstituted or substituted with $R^4$,
  (11) —S(O)$_2$—NR$^{10}$R$^{11}$,
  (12) —S(O)$_q$—R$^{12}$, where q is 0, 1 or 2 and where $R^{12}$ is selected from the definitions of $R^{10}$ and $R^{11}$,
  (13) —CO$_2$H,
  (14) —CN, and
  (15) —NO$_2$;
$R^3$ is selected from C$_{1-6}$ alkyl and C$_{3-6}$ cycloalkyl, which is unsubstituted or substituted with one or more substituents selected from $R^4$;
$R^4$ is selected from the group consisting of:
  (1) hydroxyl,
  (2) halogen,
  (3) C$_{1-6}$ alkyl,
  (4) —C$_{3-6}$cycloalkyl,
  (5) —O—C$_{1-6}$ alkyl,
  (6) —O(C=O)—C$_{1-6}$ alkyl,
  (7) —NH$_2$,
  (7) —NH—C$_{1-6}$alkyl,
  (8) —NO$_2$,
  (9) phenyl,
  (10) heterocycle,
  (11) —CO$_2$H, and
  (12) —CN;

R⁵ is selected from the group consisting of:
(1) C_{1-6} alkyl, which is unsubstituted or substituted with halogen or phenyl,
(2) C_{3-6} cycloalkyl, which is unsubstituted or substituted with C_{1-6} alkyl, halogen or phenyl, and
(3) phenyl, which is unsubstituted or substituted with C_{1-6} alkyl, halogen or phenyl;

R⁶ is selected from the group consisting of:
(1) hydrogen,
(2) halogen,
(3) C_{2-6} alkenyl,
(4) C_{3-6} cycloalkyl,
(5) —(C=O)—H, and
(6) —(C=O)—C_{1-6} alkyl;
or a pharmaceutically acceptable salt thereof.

An embodiment of the present invention includes compounds of the formula Ia:

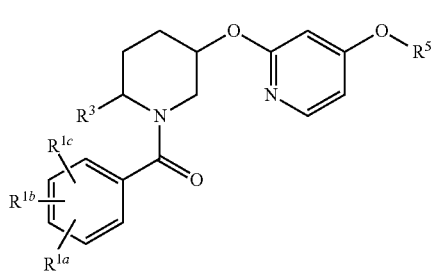

Ia wherein $R^{1a}$, $R^{1b}$, $R^{1c}$, $R^3$ and $R^5$ are defined herein; or a pharmaceutically acceptable salt thereof.

An embodiment of the present invention includes compounds of the formula Ia':

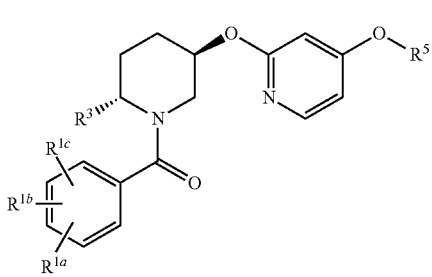

Ia' wherein $R^{1a}$, $R^{1b}$, $R^{1c}$, $R^3$ and $R^5$ are defined herein; or a pharmaceutically acceptable salt thereof.

An embodiment of the present invention includes compounds of the formula Ia":

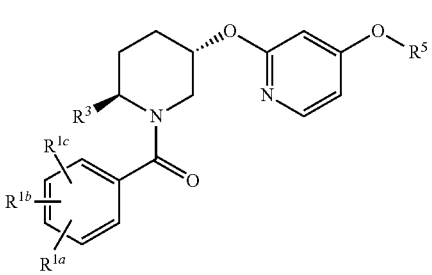

Ia"

wherein $R^{1a}$, $R^{1b}$, $R^{1c}$, $R^3$ and $R^5$ are defined herein; or a pharmaceutically acceptable salt thereof.

An embodiment of the present invention includes compounds of the formula Ib:

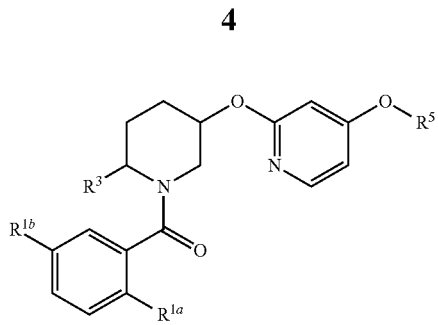

Ib wherein $R^{1a}$, $R^{1b}$, $R^3$ and $R^5$ are defined herein; or a pharmaceutically acceptable salt thereof.

An embodiment of the present invention includes compounds of the formula Ib':

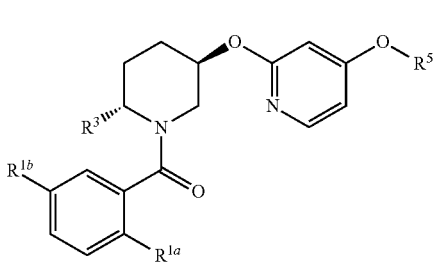

Ib' wherein $R^{1a}$, $R^{1b}$, $R^3$ and $R^5$ are defined herein; or a pharmaceutically acceptable salt thereof.

An embodiment of the present invention includes compounds of the formula Ib":

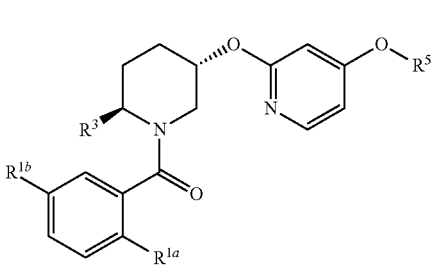

Ib"

wherein $R^{1a}$, $R^{1b}$, $R^3$ and $R^5$ are defined herein; or a pharmaceutically acceptable salt thereof.

An embodiment of the present invention includes compounds of the formula Ic:

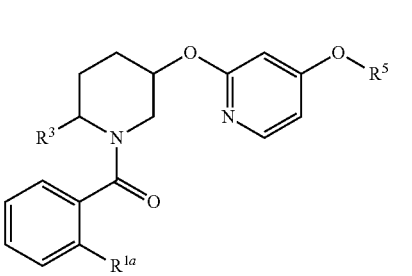

Ic wherein $R^{1a}$, $R^3$ and $R^5$ are defined herein; or a pharmaceutically acceptable salt thereof.

An embodiment of the present invention includes compounds of the formula Ic':

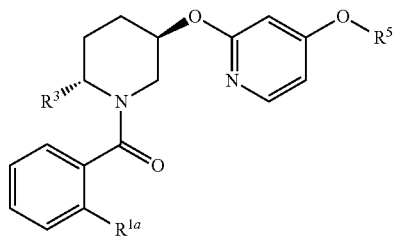

wherein $R^{1a}$, $R^3$ and $R^5$ are defined herein; or a pharmaceutically acceptable salt thereof.

An embodiment of the present invention includes compounds of the formula Ic":

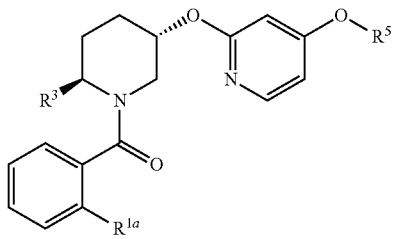

wherein $R^{1a}$, $R^3$ and $R^5$ are defined herein; or a pharmaceutically acceptable salt thereof.

An embodiment of the present invention includes compounds of the formula Id:

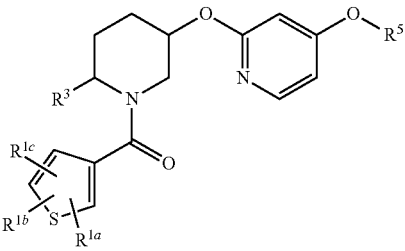

wherein $R^{1a}$, $R^{1b}$, $R^{1c}$, $R^3$ and $R^5$ are defined herein; or a pharmaceutically acceptable salt thereof.

An embodiment of the present invention includes compounds of the formula Id':

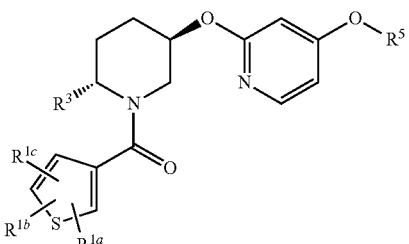

wherein $R^{1a}$, $R^{1b}$, $R^{1c}$, $R^3$ and $R^5$ are defined herein; or a pharmaceutically acceptable salt thereof.

An embodiment of the present invention includes compounds of the formula Id":

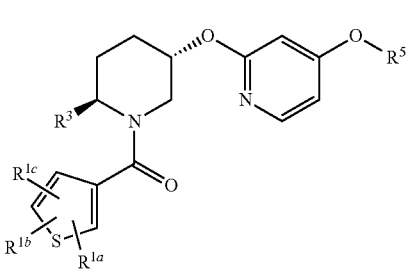

wherein $R^{1a}$, $R^{1b}$, $R^{1c}$, $R^3$ and $R^5$ are defined herein; or a pharmaceutically acceptable salt thereof.

An embodiment of the present invention includes compounds of the formula Ie:

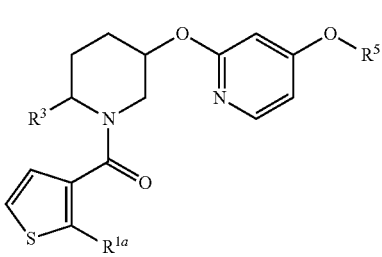

wherein $R^{1a}$, $R^3$ and $R^5$ are defined herein; or a pharmaceutically acceptable salt thereof.

An embodiment of the present invention includes compounds of the formula Ie':

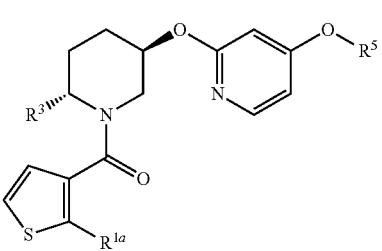

wherein $R^{1a}$, $R^3$ and $R^5$ are defined herein; or a pharmaceutically acceptable salt thereof.

An embodiment of the present invention includes compounds of the formula Ie":

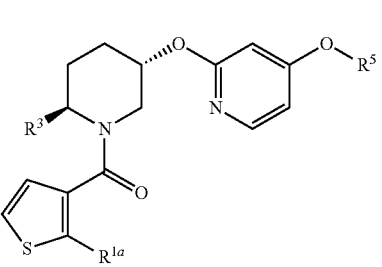

wherein $R^{1a}$, $R^3$ and $R^5$ are defined herein; or a pharmaceutically acceptable salt thereof.

An embodiment of the present invention includes compounds wherein A is selected from phenyl, pyridyl, thiophenyl, thiazolyl, isothiazolyl, and pyrazolyl. An embodiment of the present invention includes compounds wherein A is phenyl. An embodiment of the present invention includes compounds wherein A is pyridyl. An embodiment of the present invention includes compounds wherein A is thiophenyl. An embodiment of the present invention includes compounds wherein A is thiazolyl. An embodiment of the present invention includes compounds wherein A is isothiazolyl. An embodiment of the present invention includes compounds wherein A is pyrazolyl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$ alkyl, which is unsubstituted or substituted with halogen, hydroxyl or phenyl,
(5) —O—$C_{1-6}$ alkyl, which is unsubstituted or substituted with halogen, hydroxyl or phenyl,
(6) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or —$NO_2$,
(7) phenyl, which is unsubstituted or substituted with halogen, hydroxyl, $C_{1-6}$ alkyl, —O—$C_{1-6}$ alkyl or —$NO_2$,
(8) —O-phenyl, which is unsubstituted or substituted with halogen, hydroxyl, $C_{1-6}$alkyl, —O—$C_{1-6}$ alkyl or —$NO_2$,
(9) —CN, and
(10) —NH—$C_{1-6}$ alkyl, or —N($C_{1-6}$ alkyl)($C_{1-6}$ alkyl), which is unsubstituted or substituted with halogen, hydroxyl, $C_{1-6}$alkyl, and —O—$C_{1-6}$alkyl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$ alkyl, which is unsubstituted or substituted with halogen, hydroxyl or phenyl,
(5) —O—$C_{1-6}$ alkyl, which is unsubstituted or substituted with halogen, hydroxyl or phenyl,
(6) —CN, and
(7) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$ alkyl, —O—$C_{1-6}$ alkyl or —$NO_2$.

An embodiment of the present invention includes compounds wherein $R^{1a}$, $R^{1b}$ and $R^{1c}$ are independently selected from the group consisting of:
(1) hydrogen,
(2) halogen,
(3) $C_{1-6}$ alkyl, which is unsubstituted or substituted with halogen,
(4) —O—$C_{1-6}$ alkyl, which is unsubstituted or substituted with halogen,
(5) —CN, and
(6) heteroaryl, wherein heteroaryl is selected from imidazolyl, indolyl, oxazolyl, pyridyl, pyrrolyl, pyrimidinyl, tetrazolyl, and triazolyl.

An embodiment of the present invention includes compounds wherein $R^{1c}$ is hydrogen, and $R^{1a}$ and $R^{1b}$ are independently selected from the group consisting of:
(1) hydrogen,
(2) fluoro,
(3) chloro,
(4) bromo,
(5) methyl,
(6) ethyl,
(7) methoxy,
(8) trifluoromethyl, and
(9) heteroaryl, wherein heteroaryl is selected from imidazolyl, indolyl, oxazolyl, pyridyl, pyrrolyl, pyrimidinyl, tetrazolyl, and triazolyl, An embodiment of the present invention includes compounds wherein $R^{1c}$ is hydrogen, and $R^{1a}$ and $R^{1b}$ are independently selected from the group consisting of:
(1) hydrogen,
(2) fluoro,
(3) chloro,
(4) methyl,
(5) methoxy,
(6) tetrazolyl, and
(7) triazolyl.

An embodiment of the present invention includes compounds wherein $R^3$ is $C_{1-6}$ alkyl. An embodiment of the present invention includes compounds wherein $R^3$ is $C_{3-6}$ cycloalkyl. An embodiment of the present invention includes compounds wherein $R^3$ is methyl or ethyl. An embodiment of the present invention includes compounds wherein $R^3$ is methyl. An embodiment of the present invention includes compounds wherein $R^3$ is (R)-methyl.

An embodiment of the present invention includes compounds wherein $R^5$ is selected from the group consisting of:
(1) $C_{1-6}$ alkyl, which is unsubstituted or substituted with halogen or phenyl,
(2) $C_{3-6}$ cycloalkyl, which is unsubstituted or substituted with $C_{1-6}$ alkyl or halogen, and
(3) phenyl.

An embodiment of the present invention includes compounds wherein $R^5$ is selected from the group consisting of: methyl, fluoro-methyl, difluoro-methyl, ethyl, fluoroethyl, isopropyl, cyclopropyl, butyl, 2,2-difluoro-ethyl, phenyl, and benzyl.

An embodiment of the present invention includes compounds wherein $R^5$ is methyl. An embodiment of the present invention includes compounds wherein $R^5$ is ethyl. An embodiment of the present invention includes compounds wherein $R^5$ is isopropyl.

An embodiment of the present invention includes compounds wherein $R^6$ is selected from the group consisting of:
(1) hydrogen,
(2) fluoro,
(3) chloro,
(4) bromo,
(5) methyl,
(6) ethenyl,
(7) —(C=O)—H, and
(8) —(C=O)—$CH_3$.

An embodiment of the present invention includes compounds wherein $R^6$ is hydrogen.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-6}$ alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals may be treated according to the method of the present invention. The present invention is directed to a compound of the present invention or a pharmaceutically acceptable salt thereof that could be useful in medicine. The present invention may further be directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% CO2) in 60 µl assay buffer containing 1 µM Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 min and finally 25 µl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in antagonizing the human orexin-2 receptor in the aforementioned assays with an $IC_{50}$ of about 0.1 nM to 100 nM. All of the final compounds of the following examples had activity in the radioligand binding assay with a Ki of about 0.1 nM to 100 nM against the orexin-2 receptor. All of the final compounds of the following examples had activity in the FLIPR assay with an IC50 of about 0.1 nM to 100 nM against the orexin-2 receptor. Additional data is provided in the following Examples. Such a result is indicative of the intrinsic activity of the compounds in use as antagonists of orexin-1 receptor and/or the orexin-2 receptor. In general, one of ordinary skill in the art would appreciate that a substance is considered to effectively antagonize the orexin receptor if it has an IC50 of less than about 50 µM, preferably less than about 100 nM. With respect to other piperidine compounds such as those disclosed in WO 2010/048012, it would be desirable that the present compounds exhibit unexpected properties, such as increased selectivity at the orexin-2 receptor relative to the orexin-1 receptor. For example, relative to 2-pyridyloxy compounds of WO2010/048012 that do not possess a 2-pyridyloxy-4-ether substituent, the compounds of the examples possess greater selectivity for the orexin-2 receptor than for the orexin-1 receptor.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociateive disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian patient in need thereof which comprises administering to the patient a therapeutically effective amount of a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 Hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH2); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fabric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists;

(19) CCK agonists; (20) CCK-A (cholecystokinin-A) agonists, such as AR-R 15849, GI 181771, JMV-180, A-71378, A-71623 and SR14613, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide., (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptble salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a nonsteroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-azabenzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; MTBE: methyl tert-butyl ether; $NaHCO_3$: sodium bicarbonate; NaOH: sodium hydroxide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1

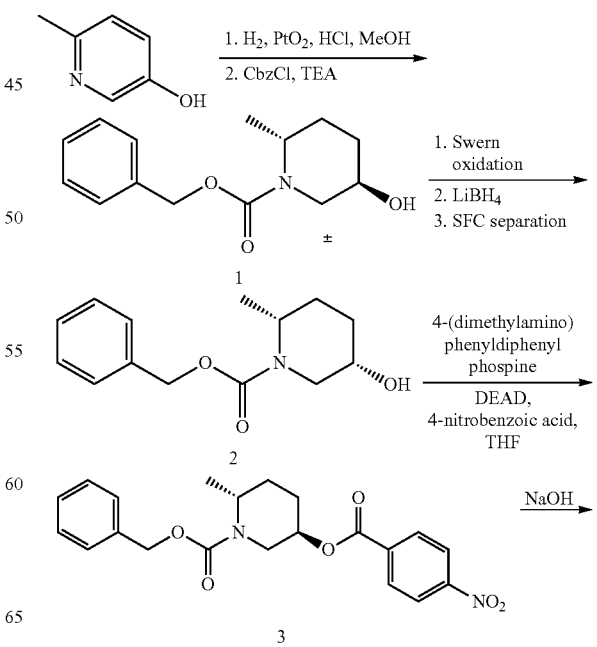

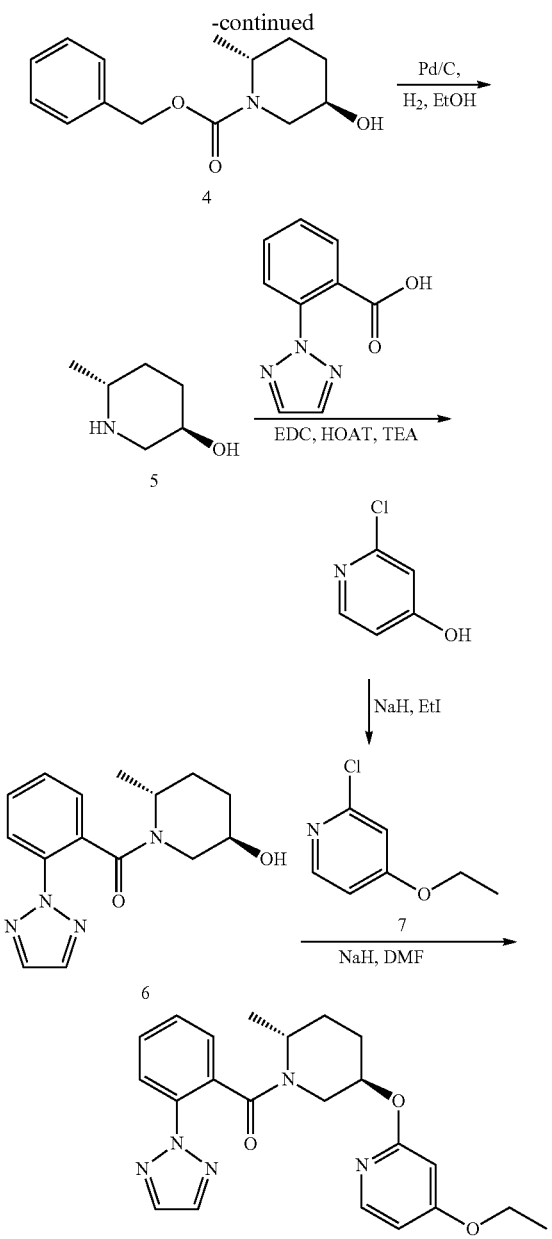

4-Ethoxy-2-{[(3R,6R)-6-methyl-1-{[2-(2H-1,2,3-triazol-2-yl)phenyl]carbonyl}piperidin-3-yl]oxy}pyridine Step 1: ±Benzyl trans-5-hydroxy-2-methylpiperidine-1-carboxylate (1)

To a solution of 6-methylpyridin-3-ol (20.0 g, 0.183 mol) in MeOH (200 mL) was added concentrated HCl (15.43 mL, 0.1850 mol) and PtO₂ (2.40 g, 0.011 mol). The resulting mixture was heated to 70° C. at 50 PSI overnight. The reaction was filtered over solka-floc to remove the PtO₂ and concentrated to a solid to provide ±trans-6-methylpiperidin-3-ol hydrochloride. The crude solid was taken on without further purification.

A mixture of ±trans-6-methylpiperidin-3-ol hydrochloride (14.0 g, 0.092 mol) in CH₂Cl₂ (150 mL) was cooled at 0° C. Triethylamine (51.5 mL, 0.369 mol) was added slowly. CbzCl (13.59 mL, 0.092 mol) was added dropwise, keeping the temperature below 20° C. The reaction was allowed to warm overnight to room temperature. The reaction was quenched by addition of water and diluted further with additional CH₂Cl₂. The layers were separated and the organics were dried over MgSO₄ and concentrated. The crude material was purified by silica gel gradient chromatography (0-75% ethyl acetate in hexanes), providing the titled compound as an oil.

Step 2: Benzyl (2R,5S)-5-hydroxy-2-methylpiperidine-1-carboxylate (2)

To a solution of oxalyl chloride (13.17 mL, 0.150 mol) in CH₂Cl₂ (250 mL) at −78° C. was added DMSO (14.23 mL, 0.201 mol) dropwise. The reaction was aged for 20 min at −78° C., then ±trans-6-methylpiperidin-3-ol hydrochloride (25.0 g, 0.100 mol) was added dropwise over 10 min and aged for an additional 10 min before the triethylamine (41.9 mL, 0.301 mol) was added dropwise over 5 min at −78° C. The reaction was warmed to room temperature, then quenched with addition of half-saturated, aqueous NaHCO₃ and additional CH₂Cl₂. The layers were separated and the organics were dried with MgSO₄ and concentrated. The crude material was purified by silica gel gradient chromatography (0-50% ethyl acetate in hexanes), providing ±benzyl 2-methyl-5-oxopiperidine-1-carboxylate as a yellow oil.

To a solution of THF (200 mL) and MeOH (11 mL) was added lithium borohydride (2 M, 89 mL, 0.18 mol). Some gas evolution and small exotherm were observed. The reaction was aged at room temperature for 30 min before being cooled to −10° C. with an acetone:ice bath. ±Benzyl 2-methyl-5-oxopiperidine-1-carboxylate (22.0 g, 0.089 mol) was then added dropwise, keeping the temperature below −5° C. The reaction was then aged at −10° C. for 30 min. The reaction was quenched by adding half-saturated, aqueous NaHCO₃, then extracted with EtOAc. The layers were separated and the organics dried with MgSO₄. The organics were concentrated to give ±benzyl-5-hydroxy-2-methylpiperidine-1-carboxylate as a crude, colorless oil. Chiral separation (SFC, IC 30×250 mm, 15% MeOH/CO₂, 70 ml/min, 115 mg/ml in MeOH) of the crude ±benzyl-5-hydroxy-2-methylpiperidine-1-carboxylate provided the titled compound as enantiopure material.

Step 3: Benzyl (2R,5R)-2-methyl-5-{[(4-nitrophenyl)carbonyl]oxy}piperidine-1-carboxylate (3)

To a THF (909 ml) solution of benzyl (2R,5S)-5-hydroxy-2-methylpiperidine-1-carboxylate (34 g, 136 mmol), 4-(dimethylamino) phenyldiphenylphosphine (58.3 g, 191 mmol), and 4-nitrobenzoic acid (29.6 g, 177 mmol) was added, under N₂, DEAD (30.0 ml, 191 mmol) dropwise at −15 to −25° C. over 20 min. The reaction was allowed to warm to RT overnight. The reaction was concentrated in vacuo, removing most THF, then diluted with Et₂O (500 mL). The mixture was cooled at 0° C. and washed with 1 N HCl (5×200 mL). The combined aqueous phases were back-extracted twice with Et₂O. The combined organic phases were subsequently washed twice more with 1 N HCl. The organics were dried over MgSO₄, filtered, and concentrated. The crude material was purified by silica gel gradient chromatography (0-40% ethyl acetate in hexanes), providing the titled compound as a light yellow oil which slowly solidified. LRMS m/z (M+H) 399.3 found, 399.1 required.

Step 4: Benzyl (2R,5R)-5-hydroxy-2-methylpiperidine-1-carboxylate (4)

To a solution of benzyl (2R,5R)-2-methyl-5-{[(4-nitrophenyl)carbonyl]oxy}piperidine-1-carboxylate (54.3 g, 136 mmol) in THF (850 mL) and MeOH (138 mL) was added 1 N NaOH (204 mL) and water (30 mL). The solution was stirred overnight, then concentrated in vacuo. The residue was diluted with minimal brine and water and extracted twice with EtOAc. The organics were washed with brine, dried over MgSO$_4$, filtered, and concentrated to give the titled compound as a crude, orange-yellow oil which was used without further purification. $^1$H NMR (400 MHz, CDCl$_3$) δ 7.28-7.36 (m, 5H), 5.14 (d, J=3.5 Hz, 2H), 4.50 (t, J=6.8 Hz, 1H), 4.09 (d, J=8.8 Hz, 1H), 3.94 (s, 1H), 3.09 (dd, J=14.3, 1.9 Hz, 1H), 2.06-2.15 (m, 1H), 1.96 (br s, 1H), 1.75-1.83 (m, 1H), 1.66-1.72 (m, 1H), 1.24-1.32 (m, 2H), 1.16 (d, J=7.0 Hz, 2H) ppm. LRMS m/z (M+H) 250.1 found, 250.1 required.

Step 5: (3R,6R)-6-Methylpiperidin-3-ol (5)

A solution of benzyl (2R,5R)-5-hydroxy-2-methylpiperidine-1-carboxylate (11.5 g, 46.1 mmol), and palladium (10 wt % on activated carbon, 3.68 g) in degassed EtOH (300 mL) was stirred for 3 nights under an atmosphere of hydrogen gas. The degassed mixture was then filtered over celite, washing with EtOH. The filtrate was concentrated to give the titled compound as a crude, white solid which was used without further purification. LRMS m/z (M+H) 116.1 found, 116.1 required.

Step 6: (2-(2H-1,2,3-Triazol-2-yl)phenyl)((2R,5R)-5-hydroxy-2-methylpiperidin-1-yl)methanone (6)

A solution of (3R,6R)-6-methylpiperidin-3-ol (5.31 g, 46.1 mmol), 2-(2H-1,2,3-triazol-2-yl)benzoic acid (10.5 g, 55.3 mmol), EDC (17.7 g, 92.0 mmol), 1-hydroxy-7-azabenzotriazole (12.6 g, 92.0 mmol), and triethylamine (19.3 mL, 138 mmol) in DMF (300 mL) was stirred at 50° C. overnight, then diluted with saturated aqueous sodium bicarbonate and extracted 3× with ethyl acetate. The organics were washed with brine, dried over magnesium sulfate, filtered, and concentrated. The crude material was purified by silica gel gradient chromatography (0-100% ethyl acetate in hexanes), providing the titled compound as a pale yellow solid. LRMS m/z (M+H) 287.3 found, 287.1 required.

Step 7: 2-Chloro-4-ethoxypyridine (7)

A solution of 2-chloropyridin-4-ol (1.50 g, 11.6 mmol) in DMF (20 mL) was treated with sodium hydride (0.602 g, 15.0 mmol). After 20 min., iodoethane (1.12 mL, 13.9 mmol) was added. After 30 min., the mixture was quenched with saturated aqueous ammonium chloride and water, and extracted 3× with ethyl acetate. The combined organic fractions were washed with brine, dried over sodium sulfate, filtered, and concentrated. The residue was purified by silica gel gradient chromatography (0-20% ethyl acetate in hexanes), providing the title compound as a white solid. LRMS m/z (M+H) 158.1 found, 158.2 required.

Step 8: 4-Ethoxy-2-{[(3R,6R)-6-methyl-1-{[2-(2H-1,2,3-triazol-2-yl)phenyl]carbonyl}piperidin-3-yl]oxy}pyridine A solution of [(2R,5R)-5-hydroxy-2-methylpiperidin-1-yl][2-(2H-1,2,3-triazol-2-yl)phenyl]methanone (0.025 g, 0.087 mmol) in DMF (1 mL) was treated with sodium hydride (3.1 mg, 0.131 mmol). After stirring ~20 minutes, 2-chloro-4-ethoxypyridine (16.5 g, 0.105 mmol) was added and the reaction was heated to 50° C. overnight. Additional sodium hydride (1.6 mg, 0.065 mmol) was added, and the reaction was heated to 80° C. for 4 h, then quenched with saturated aqueous ammonium chloride and diluted with water. The mixture was extracted 3× with ethyl acetate and the combined organic fractions were washed with brine, dried over sodium sulfate, filtered, and concentrated. The residue was purified by silica gel chromatography (0-3% methanol in dichloromethane) to provide the title compound. HRMS m/z (M+H) 408.2016 found, 408.2030 required.

TABLE 1

The following compounds were prepared using the foregoing methodology and general procedure described in Example 1, but substituting the appropriate 2-halopyridine for 2-chloro-4-ethoxypyridine, as described in the foregoing Reaction Schemes and Examples. The requisite starting materials were commercially available, described in the literature or readily synthesized by one skilled in the art of organic synthesis from commercially available reagents using conventional reactions without undue experimentation.

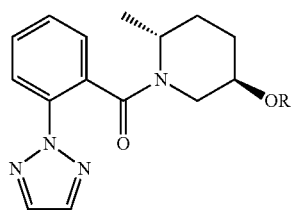

| Example | R | Name | LRMS or HRMS (M + H$^+$) |
|---------|---|------|--------------------------|

TABLE 1-continued

| | | | |
|---|---|---|---|
| 2 | 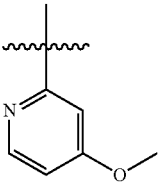 [SMILES: *c1cc(OC)ccn1] | 4-methoxy-2-{[(3R,6R)-6-methyl-1-{[2-(2H-1,2,3-triazol-2-yl)phenyl]carbonyl}piperidin-3-yl]oxy}pyridine | Calc'd 394.1876, found 394.1871 |
| 3 | 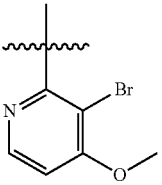 [SMILES: *c1nccc(OC)c1Br] | 3-bromo-4-methoxy-2-{[(3R,6R)-6-methyl-1-{[2-(2H-1,2,3-triazol-2-yl)phenyl]carbonyl}piperidin-3-yl]oxy}pyridine | Calc'd 472.0981, found 472.0983 |
| 4 | 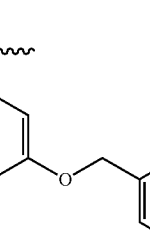 | 4-(benzyloxy)-2-{[(3R,6R)-6-methyl-1-{[2-(2H-1,2,3-triazol-2-yl)phenyl]carbonyl}piperidin-3-yl]oxy}pyridine | Calc'd 470.2188, found 470.2201 |

EXAMPLE 5

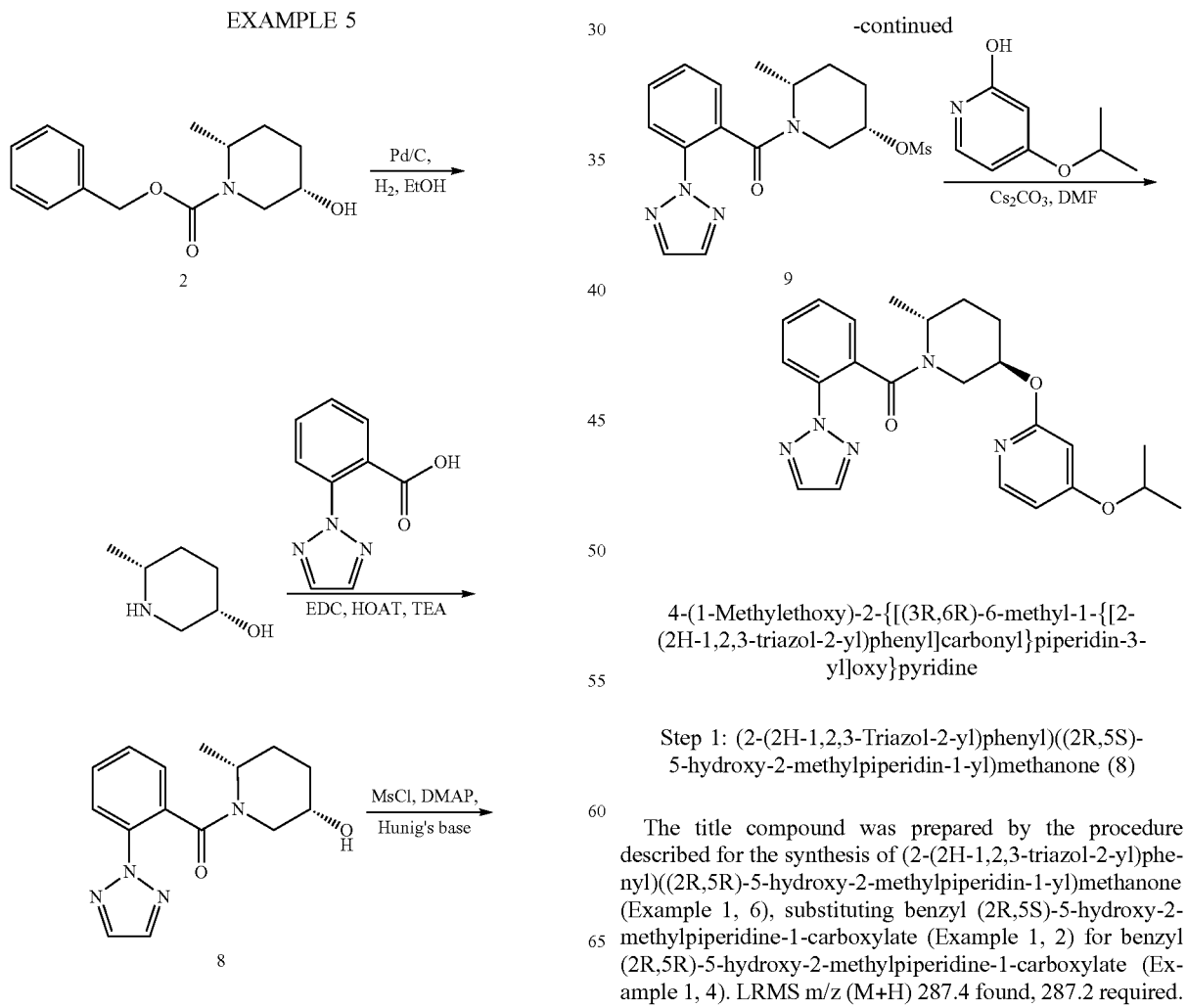

4-(1-Methylethoxy)-2-{[(3R,6R)-6-methyl-1-{[2-(2H-1,2,3-triazol-2-yl)phenyl]carbonyl}piperidin-3-yl]oxy}pyridine Step 1: (2-(2H-1,2,3-Triazol-2-yl)phenyl)((2R,5S)-5-hydroxy-2-methylpiperidin-1-yl)methanone (8)

The title compound was prepared by the procedure described for the synthesis of (2-(2H-1,2,3-triazol-2-yl)phenyl)((2R,5R)-5-hydroxy-2-methylpiperidin-1-yl)methanone (Example 1, 6), substituting benzyl (2R,5S)-5-hydroxy-2-methylpiperidine-1-carboxylate (Example 1, 2) for benzyl (2R,5R)-5-hydroxy-2-methylpiperidine-1-carboxylate (Example 1, 4). LRMS m/z (M+H) 287.4 found, 287.2 required.

Step 2: (3S,6R)-1-(2-(2H-1,2,3-Triazol-2-yl)benzoyl)-6-methylpiperidin-3-yl methanesulfonate (9)

A solution of 2-(2H-1,2,3-triazol-2-yl)phenyl)((2R,5S)-5-hydroxy-2-methylpiperidin-1-yl)methanone (0.300 g, 1.05 mmol), 4-dimethylaminopyridine (0.013 g, 0.10 mmol), and Hunig's base (0.27 mL, 0.0016 mmol) in dichloromethane (10.5 mL) was cooled to 0° C. and treated with methanesulfonyl chloride (0.10 mL, 0.0013 mmol). After 3 hours, the mixture was poured into saturated aqueous sodium bicarbonate and extracted 2× with dichloromethane. The combined organic fractions were washed with brine, dried over sodium sulfate, filtered, and concentrated in vacuo, providing the title compound as a sticky off-white foam which was used without further purification. LRMS m/z (M+H) 365.3 found, 365.2 required.

Step 3: 4-(1-Methylethoxy)-2-{[(3R,6R)-6-methyl-1-{[2-(2H-1,2,3-triazol-2-yl)phenyl]carbonyl}piperidin-3-yl]oxy}pyridine A solution of (3S,6R)-1-(2-(2H-1,2,3-triazol-2-yl)benzoyl)-6-methylpiperidin-3-yl methanesulfonate (0.020 g, 0.055 mmol) and 4-isopropoxypyridin-2-ol (0.033 g, 0.22 mmol) in DMF (0.5 mL) was treated with cesium carbonate (0.036 g, 0.11 mmol) and heated to 100° C. overnight. The mixture was filtered and purified by reverse phase preparatory HPLC, providing the title compound. HRMS m/z (M+H) 422.2187 found, 422.2188 required.

EXAMPLE 6

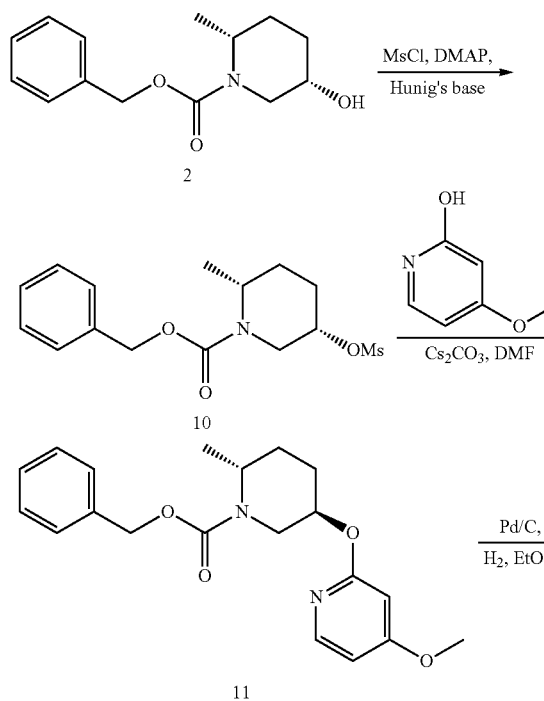

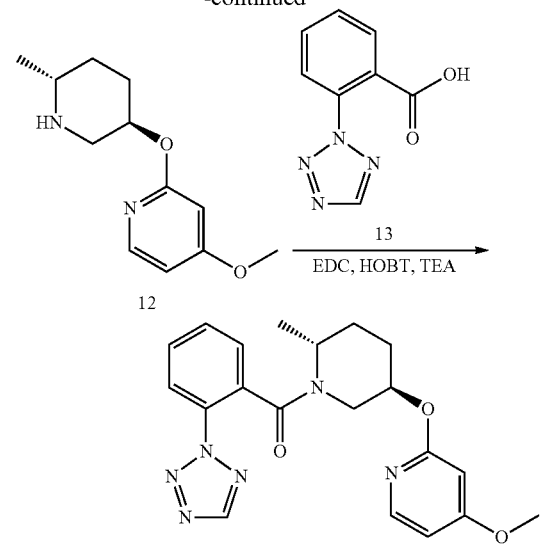

4-Methoxy-2-{[(3R,6R)-6-methyl-1-{[2-(2H-tetrazol-2-yl)phenyl]carbonyl}piperidin-3-yl]oxy}pyridine

Step 1: (2R,5S)-Benzyl 2-methyl-5-((methylsulfonyl)oxy)piperidine-1-carboxylate (10)

A solution (2R,5S)-benzyl 5-hydroxy-2-methylpiperidine-1-carboxylate (Example 1, 2, 10.0 g, 40.1 mmol), 4-dimethylaminopyridine (0.490 g, 4.01 mmol), and Hunig's base (10.5 mL, 60.2 mmol) in dichloromethane (200 mL) was cooled to 0° C. and treated with a solution of methanesulfonyl chloride (3.91 mL, 50.1 mmol) in dichloromethane (67 mL) dropwise. After 2 hours, the mixture was diluted with water and 1 N HCl to pH ~5. The organic fraction was washed with brine, dried over magnesium sulfate, filtered, and concentrated, providing the title compound as an orange oil which was used without further purification. LRMS m/z (M+H) 328.3 found, 328.2 required.

Step 2: (2R,5R)-Benzyl 5-((4-methoxypyridin-2-yl)oxy)-2-methylpiperidine-1-carboxylate (11)

A solution of (2R,5S)-benzyl 2-methyl-5-((methylsulfonyl)oxy)piperidine-1-carboxylate (0.800 g, 2.44 mmol) in DMF (10 mL) was treated with 4-methoxypyridin-2-ol (0.459 g, 3.67 mmol) and cesium carbonate (0.876 g, 2.69 mmol) and heated at 100° C. overnight. The reaction was diluted with saturated aqueous sodium bicarbonate and extracted 2× with ethyl acetate. The combined organic fractions were washed with brine, dried over sodium sulfate, filtered, and concentrated in vacuo. The residue was purified by silica gel gradient chromatography (0-50% ethyl acetate in hexanes), providing the title compound LRMS m/z (M+H) 357.3 found, 357.3 required.

Step 3: 4-Methoxy-2-(((3R,6R)-6-methylpiperidin-3-yl)oxy)pyridine (12)

A solution of (2R,5R)-benzyl 5-((4-methoxypyridin-2-yl)oxy)-2-methylpiperidine-1-carboxylate (0.730 g, 2.048 mmol) and palladium (10 wt % on activated carbon, 0.011 g, 0.10 mmol) in degassed methanol (10 mL) was stirred overnight under an atmosphere of hydrogen gas. The degassed mixture was then filtered over celite, washing with methanol. The filtrate was concentrated in vacuo, providing the title compound which was used without further purification. LRMS m/z (M+H) 223.3 found, 223.3 required.

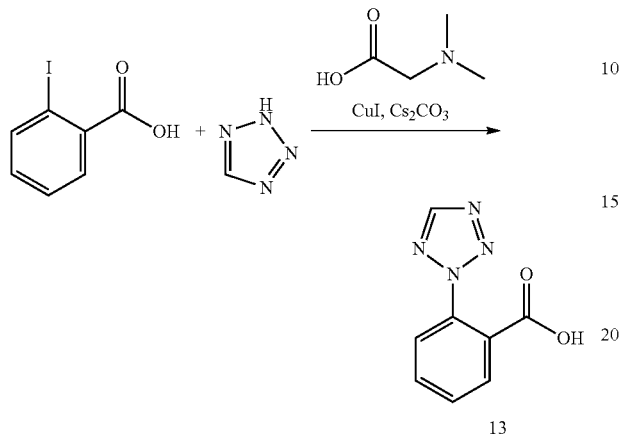

Step 4: 2-(2H-Tetrazol-2-yl)benzoic acid (13)

To a 20 mL microwave tube was charged 2-iodobenzoic acid (1.85 g, 7.46 mmol), cesium carbonate (4.06 g, 12.5 mmol), copper(I) iodide (0.128 g, 0.671 mmol), and DMA (8.0 mL). N,N'-Dimethylglyine (0.131 g, 1.27 mmol) and tetrazole (1.29 g, 18.4 mmol) were added, and the solution was irradiated in a microwave reactor at 100° C. for 1 hour. The reaction was diluted with water and 1 N aqueous sodium hydroxide and washed with ethyl acetate. The aqueous fraction was acidified with conc. HCl and extracted 2× with ethyl acetate. The combined organic fractions were washed with brine, dried over magnesium sulfate, filtered, and concentrated. The residue was purified by silica gel gradient chromatography [0-85% (1% acetic acid in ethyl acetate) in hexanes], providing the title compound. $^1$H NMR (400 MHz, CD$_3$OD): δ 7.72-7.84 (m, 3 H), 8.07 (dd, J=7.6, 1.6 Hz, 1 H), 8.90 (s, 1 H) ppm. LRMS m/z (M+H) 191.1 found, 191.2.

Step 5: 4-Methoxy-2-{[(3R,6R)-6-methyl-1-{[2-(2H-tetrazol-2-yl)phenyl]carbonyl}piperidin-3-yl]oxy}pyridine A solution of 4-methoxy-2-(((3R,6R)-6-methylpiperidin-3-yl)oxy)pyridine (0.016 g, 0.063 mmol), 2-(2H-tetrazol-2-yl)benzoic acid (0.010 g, 0.053 mmol), EDC (0.015 g, 0.079 mmol), N-hydroxybenzotriazole (0.80 mg, 0.0053 mmol), and triethylamine (0.018 mL, 0.13 mmol) in DMF (0.5 mL) was heated at 50° C. for 4.5 h. The mixture was filtered and purified by reverse phase preparatory HPLC, providing the titled compound. HRMS m/z (M+H) 395.1812 found, 395.1829 required.

Alternative Procedure A to Intermediate 12

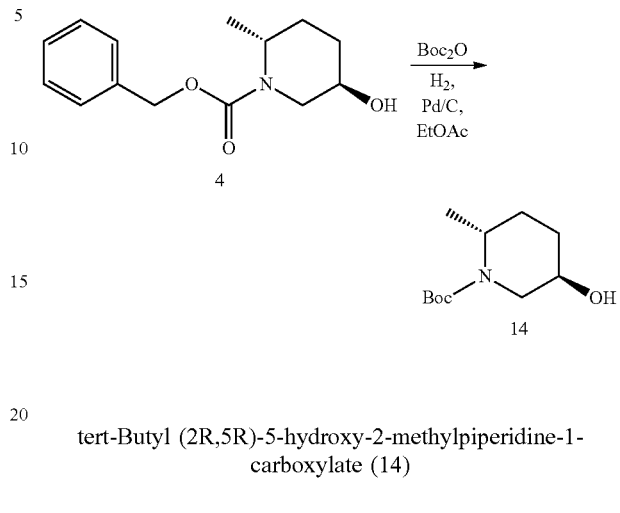

tert-Butyl (2R,5R)-5-hydroxy-2-methylpiperidine-1-carboxylate (14)

A solution of benzyl (2R,5R)-5-hydroxy-2-methylpiperidine-1-carboxylate (Example 1, 4, 34.76 g, 139 mmol), di-tert-butyl dicarbonate (33.5 g, 153 mmol), and palladium (10 wt % on activated carbon, 1.0 g) in degassed EtOAc (500 mL) was stirred overnight under an atmosphere of hydrogen gas. Additional palladium (0.2 g) was added and stirring continued for 3.5 h. The degassed mixture was filtered over celite, washing with EtOAc. The filtrate was concentrated and purified by silica gel gradient chromatography (0-75% EtOAc in hexanes), providing the titled compound as a light yellow solid. $^1$H NMR (400 MHz, CDCl$_3$) δ 4.40 (t, J=6.8 Hz, 1H), 3.86-4.05 (m, 2H), 3.02 (dd, J=14.2, 1.8 Hz, 1H), 2.22 (s, 1H), 2.01-2.13 (m, 1H), 1.59-1.82 (m, 2H) ppm. LRMS m/z (M+H) 216.3 found, 216.2 required.

Alternative Procedure B to Intermediate 12

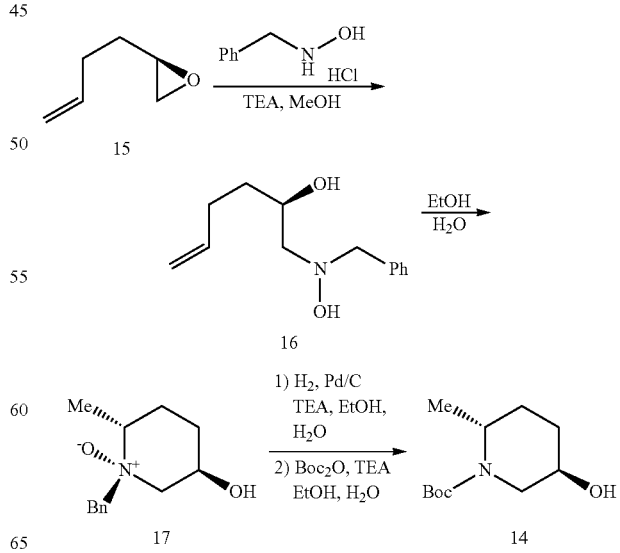

tert-Butyl (2R,5R)-5-hydroxy-2-methylpiperidine-1-carboxylate (14)

Step 1: (R)-1-(Benzyl(hydroxy)amino)hex-5-en-2-ol (16)

To a solution of (R)-1,2-epoxy-5-hexene (36.9 g, 376 mmol) and N-benzylhydroxylamine hydrochloride (50 g, 313 mmol) in degassed methanol (500 mL) was added triethylamine (31.7 g, 313 mmol) (see O'Neil, et al., Tet. Lett., 39, 9089-9092 (1998), O'Neil, et al., Synlett, 5, 695-697 (2000)). The resulting mixture was stirred, under a nitrogen atmosphere, at ambient temperature for 4 days. The reaction was quenched with 5 wt % aqueous NaHCO$_3$ and then extracted 2× with EtOAc. The combined organic layers were concentrated, removing the aqueous phase that separated out part-way through the concentration, to afford the title compound as a crude yellow oil which was used directly in the next step, without further purification.

Step 2: (1S,2R,5R)-1-Benzyl-5-hydroxy-2-methylpiperidine 1-oxide (17)

A solution of (R)-1-(benzyl(hydroxy)amino)hex-5-en-2-ol (63.1 g, 285 mmol) in degassed ethanol (316 mL) and water (316 mL) was stirred, under a nitrogen atmosphere, at approx. 80° C. for 3 nights. The reaction mixture was then partially concentrated to remove the ethanol, and the resulting aqueous solution was washed 5× with CH$_2$Cl$_2$. The resulting crude aqueous solution of the title compound was used directly in the next step, without further purification.

Step 3: tert-Butyl (2R,5R)-5-hydroxy-2-methylpiperidine-1-carboxylate (14)

To an aqueous solution (252 mL) of (1S,2R,5R)-1-benzyl-5-hydroxy-2-methylpiperidine 1-oxide (27.8 g, 125 mmol) was added triethylamine (15.2 g, 151 mmol), ethanol (250 mL), and palladium (20 wt % on activated carbon, 2.8 g). The mixture was stirred overnight under an atmosphere of hydrogen gas (5 barg) at 50° C. The catalyst was then removed by filtration, washing with ethanol. To the resulting aqueous ethanol solution (525 mL) of (3R,6R)-6-methylpiperidin-3-ol was added triethylamine (12.7 g, 125 mmol) followed by a solution of di-tert-butyl dicarbonate (30.1 g, 138 mmol) in ethanol (29 mL). The reaction was stirred overnight at ambient temperature, and then concentrated to a volume of approx. 250 mL. The mixture was seeded with a small amount of title compound, aged at ambient temperature, concentrated to approx. 150 mL, and then cooled to 0° C. The resulting slurry was filtered, washing the solid with water. The resulting solid was dried to afford the title compound as a white solid. $^1$H NMR (400 MHz, CDCl$_3$) δ 4.35-4.46 (m, 1H), 3.98 (d, J=14.5 Hz, 1H), 3.92 (br s, 1H), 3.03 (d, J=14.5 Hz, 1H), 2.01-2.13 (m, 2H), 1.61-1.82 (m, 2H), 1.46 (s, 9H), 1.29 (br d, J=12.5 Hz, 1H), 1.13 (d, J=7.0 Hz, 3H) ppm.

Completion of Alternative Route to Intermediate 12:

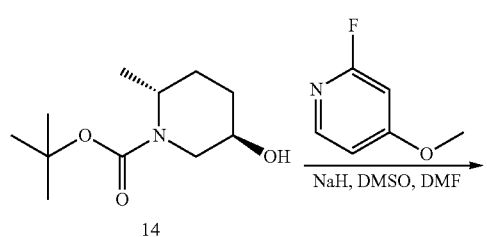

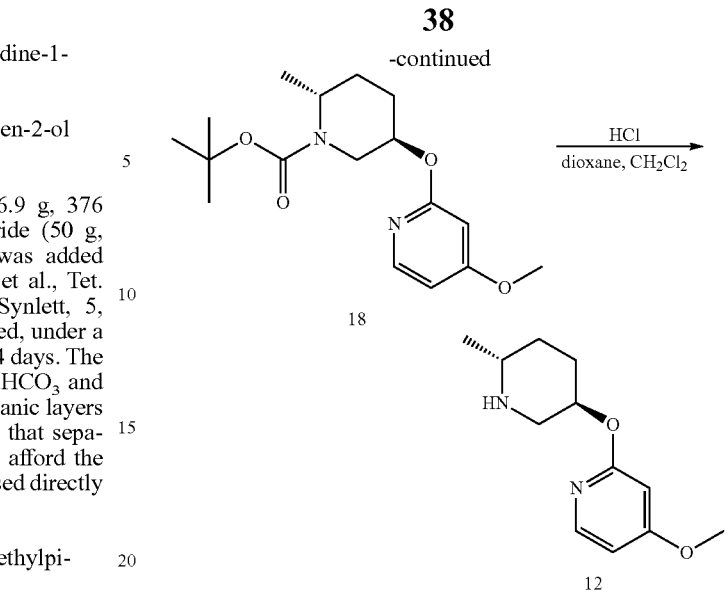

Step 1: (2R,5R)-tert-butyl 5-((4-methoxypyridin-2-yl)oxy)-2-methylpiperidine-1-carboxylate (18)

A solution of (2R,5R)-tert-butyl 5-hydroxy-2-methylpiperidine-1-carboxylate (2.50 g, 11.6 mmol) in DMSO (23 ml) and DMF (3.8 ml) was treated with NaH (dry powder, 0.56 g, 23 mmol). After stirring for ~15 mins, 2-fluoro-4-methoxypyridine (2.21 g, 17.4 mmol) was added and the reaction was heated at 50° C. overnight. The cooled reaction was quenched with saturated, aqu. NaHCO$_3$, diluted with water, and extracted 2× with EtOAc. The combined organics were washed with brine, dried over MgSO$_4$, filtered, concentrated, dried, and purified by silica gel gradient chromatography (0-40% EtOAc in hexanes), providing the titled compound as a colorless oil. $^1$H NMR (400 MHz, CDCl$_3$) δ 7.91 (d, J=5.8 Hz, 1H), 6.44 (dd, J=2.4, 5.8 Hz, 1H), 6.17 (d, J=2.4 Hz, 1H), 5.11 (br s, 1H), 4.53 (br s, 1H), 4.35 (d, J=14.8 Hz, 1H), 3.79 (s, 3H), 3.05 (dd, J=1.6, 14.8 Hz, 1 H), 2.12-2.17 (m, 1H), 1.88-1.92 (m, 2H), 1.30 (s, 9H), 1.18-1.35 (m, 1H), 1.18 (d, J=6.8 Hz, 3H) ppm. LRMS m/z (M+H) 323.5 found, 323.4 required.

Step 2: 4-methoxy-2-(((3R,6R)-6-methylpiperidin-3-yl)oxy)pyridine (12)

A solution of (2R,5R)-tert-butyl 5-((4-methoxypyridin-2-yl)oxy)-2-methylpiperidine-1-carboxylate (3.73 g, 11.6 mmol in CH$_2$Cl$_2$ (5.4 ml) was cooled at −78° C. and treated with HCl, 4 M in dioxane (20.3 mL). The reaction was allowed to warm to RT and stirred overnight, then concentrated in vacuo. The residue was taken up in EtOAc and free-based by addition of 1 N NaOH. The layers were separated and the aqueous portion was extracted 2× more with EtOAc. The combined organics were washed with brine, dried over MgSO4, filtered, concentrated. The crude material was purified by silica gel gradient chromatography (0-25% MeOH in CH$_2$Cl$_2$), providing the titled compound as a colorless oil. $^1$H NMR (400 MHz, CDCl$_3$) δ 7.92 (d, J=6.0 Hz, 1H), 6.44 (dd, J=2.4, 6.0 Hz, 1H), 6.15 (d, J=2.4 Hz, 1H), 4.90-4.98 (m, 1H), 3.79 (s, 3H), 3.38-3.49 (m, 1H), 2.59-2.70 (m, 2H), 2.19-2.25 (m, 1H), 1.77-1.83 (m, 1H), 1.49-1.59 (m, 1H), 1.22-1.33 (m, 1H), 1.10 (d, J=6.4 Hz, 3H) ppm. LRMS m/z (M+H) 223.1 found, 223.3 required.

TABLE 2

The following compounds were prepared using the foregoing methodology and general procedure described in Example 6, but substituting the appropriate carboxylic acid for 2-(2H-tetrazol-2-yl) benzoic acid, and substituting the appropriate 2-hydroxypyridine for 4-methoxypyridin-2-ol (via first scheme with intermediate 10) or 2-fluoropyridine for 2-fluoro-4-methoxypyridine (via alternate scheme with intermediate 14), as described in the foregoing Reaction Schemes and Examples. The requisite starting materials were commercially available, described in the literature or readily synthesized by one skilled in the art of organic synthesis from commercially available reagents using conventional reactions without undue experimentation.

| Example | R | R' | Name | LRMS or HRMS (M + H⁺) |
|---|---|---|---|---|
| 7 | (2-(2H-tetrazol-2-yl)phenyl)carbonyl | iPr | 4-(1-methylethoxy)-2-{[(3R,6R)-6-methyl-1-{[2-(2H-tetrazol-2-yl)phenyl]carbonyl}piperidin-3-yl]oxy}pyridine | Calc'd 423.2141, found 423.2125 |
| 8 | (2-(2H-tetrazol-2-yl)phenyl)carbonyl | Et | 4-ethoxy-2-{[(3R,6R)-6-methyl-1-{[2-(2H-tetrazol-2-yl)phenyl]carbonyl}piperidin-3-yl]oxy}pyridine | Calc'd 409.1985, found 409.1970 |
| 9 | [4-(2H-1,2,3-triazol-2-yl)pyridin-3-yl]carbonyl | Me | 4-methoxy-2-{[(3R,6R)-6-methyl-1-{[4-(2H-1,2,3-triazol-2-yl)pyridin-3-yl]carbonyl}piperidin-3-yl]oxy}pyridine | Calc'd 395.1829, found 395.1838 |
| 10 | [3-fluoro-2-(2H-1,2,3-triazol-2-yl)phenyl]carbonyl | Me | 2-{[(3R,6R)-1-{[3-fluoro-2-(2H-1,2,3-triazol-2-yl)phenyl]carbonyl}-6-methylpiperidin-3-yl]oxy}-4-methoxypyridine | Calc'd 412.1782, found 412.1786 |
| 11 | [4-carbamoyl-2-(2H-1,2,3-triazol-2-yl)phenyl]carbonyl | Me | 3-({(2R,5R)-5-[(4-methoxypyridin-2-yl)oxy]-2-methylpiperidin-1-yl}carbonyl)-4-(2H-1,2,3-triazol-2-yl)benzamide | Calc'd 437.1934, found 437.1935 |
| 12 | (2-cyclopropylphenyl)carbonyl | Me | 2-({(3R,6R)-1-[(2-cyclopropylphenyl)carbonyl]-6-methylpiperidin-3-yl}oxy)-4-methoxypyridine | Calc'd 367.2018, found 367.2024 |
| 13 | [2-(trifluoromethyl)phenyl]carbonyl | Me | 4-methoxy-2-{[(3R,6R)-6-methyl-1-{[2-(trifluoromethyl)phenyl]carbonyl}piperidin-3-yl]oxy}pyridine | Calc'd 395.158, found 395.1581 |
| 14 | [2-(methoxymethyl)phenyl]carbonyl | Me | 2-({(3R,6R)-1-[(2-ethoxyphenyl)carbonyl]-6-methylpiperidin-3-yl}oxy)-4-methoxypyridine | Calc'd 371.1967, found 371.1973 |
| 15 | (6-methoxy-2-phenylpyridin-3-yl)carbonyl | Me | 6-methoxy-3-({(2R,5R)-5-[(4-methoxypyridin-2-yl)oxy]-2-methylpiperidin-1-yl}carbonyl)-2-phenylpyridine | Calc'd 434.2076, found 434.2082 |
| 16 | (4-phenylisothiazol-5-yl)carbonyl | Me | 4-methoxy-2-({(3R,6R)-6-methyl-1-[(4-phenylisothiazol-5-yl)carbonyl]piperidin-3-yl}oxy)pyridine | Calc'd 410.1535, found 410.1537 |
| 17 | [2-fluoro-6-(2H-1,2,3-triazol-2-yl)phenyl]carbonyl | Me | 2-{[(3R,6R)-1-{[2-fluoro-6-(2H-1,2,3-triazol-2-yl)phenyl]carbonyl}-6-methylpiperidin-3-yl]oxy}-4-methoxypyridine | Calc'd 412.1779, found 412.1786 |

TABLE 2-continued

| | | | | |
|---|---|---|---|---|
| 18 | [structure] | Me | 6-methoxy-3-({(2R,5R)-5-[(4-methoxypyridin-2-yl)oxy]-2-methylpyridin-1-yl}carbonyl)-2-(2H-1,2,3-triazol-2-yl)pyridine | Calc'd 425.1934, found 425.1938 |
| 19 | [structure] | Me | 2-{[(3R,6R)-1-{[4-fluoro-2-(2H-1,2,3-triazol-2-yl)phenyl]carbonyl}-6-methylpiperidin-3-yl]oxy}-4-methoxypyridine | Calc'd 412.1782, found 412.1781 |
| 20 | [structure] | Me | 4-methoxy-2-{[(3R,6R)-1-{[4-methoxy-2-(2H-1,2,3-triazol-2-yl)phenyl]carbonyl}-6-methylpiperidin-3-yl]oxy}pyridine | Calc'd 424.1982, found 424.1979 |
| 21 | [structure] | Me | 2-cyclopropyl-6-methoxy-3-({(2R,5R)-5-[(4-methoxypyridin-2-yl)oxy]-2-methylpiperidin-1-yl}carbonyl)pyridine | Calc'd 398.2076, found 398.2083 |
| 22 | [structure] | Me | 2-chloro-6-methoxy-3-({(2R,5R)-5-[(4-methoxypyridin-2-yl)oxy]-2-methylpiperidin-1-yl}carbonyl)pyridine | Calc'd 392.1374, found 392.1380 |
| 23 | [structure] | iPr | 2-{[(3R,6R)-1-{[4-fluoro-2-(2H-1,2,3-triazol-2-yl)phenyl]carbonyl}-6-methylpiperidin-3-yl]oxy}-4-(1-methylethoxy)pyridine | Calc'd 440.2095, found 440.2078 |
| 24 | [structure] | iPr | 2-{[(3R,6R)-1-{[4-methoxy-2-(2H-1,2,3-triazol-2-yl)phenyl]carbonyl}-6-methylpiperidin-3-yl]oxy}-4-(1-methylethoxy)pyridine | Calc'd 452.2294, found 452.2276 |
| 25 | [structure] | iPr | 6-methoxy-3-{[(2R,5R)-2-methyl-5-{[4-(1-methylethoxy)pyridin-2-yl]oxy}piperidin-1-yl]carbonyl}-2-(2H-1,2,3-triazol-2-yl)pyridine | Calc'd 453.2246, found 453.2230 |
| 26 | [structure] | iPr | 2-{[(3R,6R)-1-{[5-fluoro-2-(2H-1,2,3-triazol-2-yl)phenyl]carbonyl}-6-methylpiperidin-3-yl]oxy}-4-(1-methylethoxy)pyridine | Calc'd 440.2095, found 440.2078 |

EXAMPLE 27

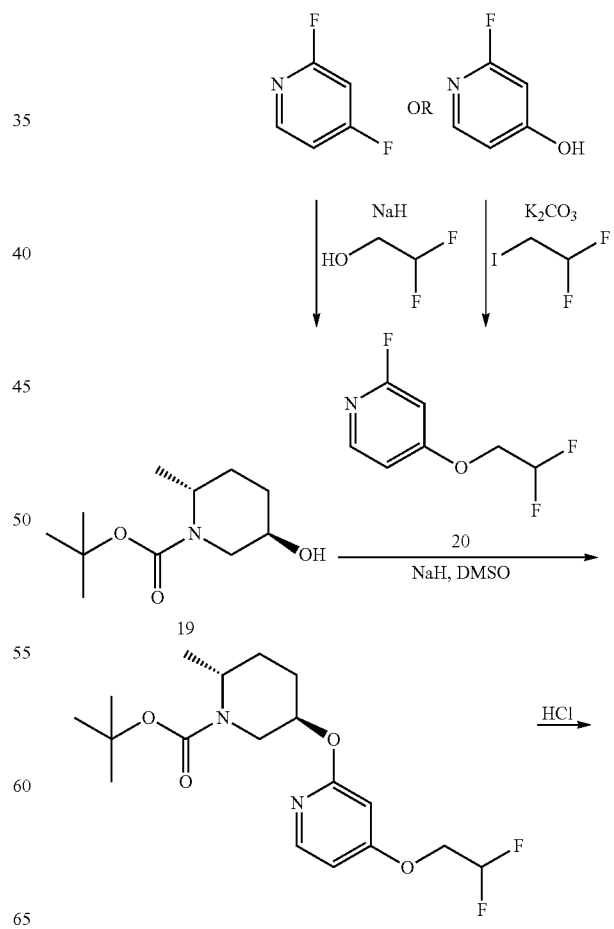

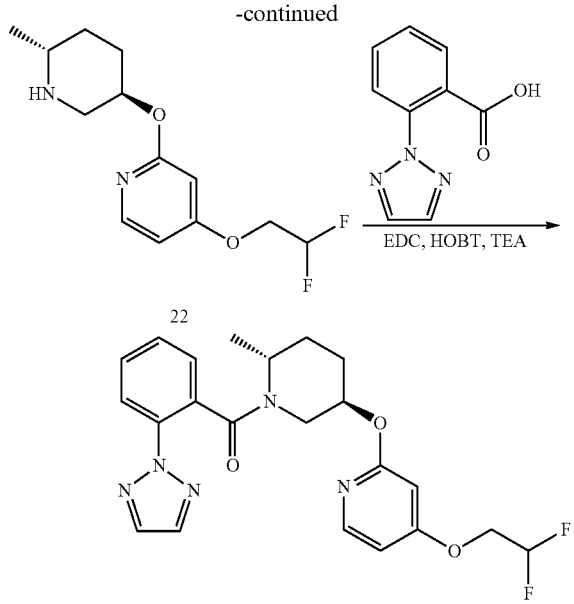

(2-(2H-1,2,3-triazol-2-yl)phenyl)((2R,5R)-5-((4-(2,2-difluoroethoxy)pyridin-2-yl)oxy)-2-methylpiperidin-1-yl)methanone Step 1: 4-(2,2-difluoroethoxy)-2-fluoropyridine (20, Method A)

A solution of 2,2-difluoroethanol (5.25 g, 64.0 mmol) and 2,4-difluoropyridine (10.5 g, 91.0 mmol) in DMF (107 ml), cooled at 0° C., was treated with NaH (dry powder, 1.69 g, 70.4 mmol) in 4 portions. After addition was complete, the reaction was maintained at 0° C. overnight. The reaction was carefully quenched by slow addition of saturated, aqu. NaHCO$_3$, then water. The solution was extracted 3× with EtOAc and the combined organics were washed with brine, dried over MgSO$_4$, filtered, and concentrated. The crude material was purified by silica gel gradient chromatography (0-20% EtOAc in hexanes), providing the titled compound as a colorless oil. $^1$H NMR (400 MHz, CDCl$_3$) δ 8.08 (d, J=6.0 Hz, 1H), 6.75-6.77 (m, 1H), 6.42 (d, J=2.0 Hz, 1H), 6.11 (tt, J=54.8, 4.0 Hz, 1H), 4.25 (dt, J=12.8, 4.0 Hz, 2H) ppm. LRMS m/z (M+H) 178.0 found, 178.1 required.

Step 1: 4-(2,2-difluoroethoxy)-2-fluoropyridine (20, Method B)

A solution of 2-fluoropyridin-4-ol (750 mg, 6.63 mmol) in DMF (20 mL) was treated with 1,1-difluoro-2-iodoethane (1655 mg, 8.62 mmol) and K$_2$CO$_3$ (1375 mg, 9.95 mmol) and heated at 60° C. overnight. The reaction was diluted with EtOAc and washed with saturated, aqu. NaHCO$_3$, then with brine. The organics were dried over MgSO$_4$, filtered, and concentrated. The crude material was purified by silica gel gradient chromatography (0-30% EtOAc in hexanes), providing the titled compound as a colorless oil.

Step 2: (2R,5R)-tert-butyl 5-((4-(2,2-difluoroethoxy)pyridin-2-yl)oxy)-2-methylpiperidine-1-carboxylate (21)

A solution of (2R,5R)-tert-butyl 5-hydroxy-2-methylpiperidine-1-carboxylate (7.30 g, 33.9 mmol) in THF (75 ml) was cooled to 15° C. KOtBu (1 M in THF, 37.3 ml) was added slowly via addition funnel while maintaining the reaction temperature below 20° C. When addition was complete, the reaction was stirred for 25 mins while warming to RT, then re-cooled in a water bath while adding 4-(2,2-difluoroethoxy)-2-fluoropyridine (6.00 g, 33.9 mmol) in THF (38 ml) quickly dropwise. The reaction temperature was maintained below 25° C. during addition. When addition was complete, the reaction was warmed to RT. After ~40 mins, the reaction was cooled at 0° C. and quenched by addition of saturated, aqu. NH$_4$Cl. The solution was extracted 2× with EtOAc and the combined organics were washed with brine, dried over MgSO$_4$, filtered, and concentrated. The crude material was purified by silica gel gradient chromatography (0-50% EtOAc in hexanes), providing the titled compound as a white solid. $^1$H NMR (400 MHz, CDCl$_3$) δ 7.96 (d, J=6.0 Hz, 1H), 6.48 (dd, J=5.6, 2.0 Hz, 1H), 6.17 (d, J=3.2 Hz, 1H), 6.08 (tt, J=54.8, 4.0 Hz, 1H), 5.12 (br s, 1H), 4.51 (br s, 1H), 4.34 (d, J=14.8 Hz, 1H), 4.09-4.20 (m, 2H), 3.05 (dd, J=14.4, 1.6 Hz, 1H), 2.10-2.18 (m, 1H), 1.88-1.92 (m, 2H), 1.24-1.36 (m, 10H), 1.18 (d, J=6.8 Hz, 3H) ppm. LRMS m/z (M+H) 373.2 found, 373.4 required.

Step 3: 4-(2,2-difluoroethoxy)-2-(((3R,6R)-6-methylpiperidin-3-yl)oxy)pyridine (22)

A solution of (2R,5R)-tert-butyl 5-((4-(2,2-difluoroethoxy)pyridin-2-yl)oxy)-2-methylpiperidine-1-carboxylate (9.61 g, 25.8 mmol) in CH$_2$Cl$_2$ (12 ml) was cooled at −78° C. and treated with HCl (4 M in dioxane, 45 mL). The reaction was warmed to RT. After ~30 mins, the reaction was concentrated in vacuo. The residue was basified by addition of 1 N NaOH and extracted 2× with EtOAc. The combined organics were washed with brine, dried over MgSO$_4$, filtered, and concentrated. The crude material was purified by silica gel gradient chromatography (0-25% MeOH in CH$_2$Cl$_2$), providing the titled compound as a colorless oil. $^1$H NMR (400 MHz, CDCl$_3$) δ 7.96 (d, J=6.0 Hz, 1H), 6.46 (dd, J=6.0, 2.4 Hz, 1H), 6.15 (d, J=2.4 Hz, 1H), 6.08 (tt, J=54.8, 4.0 Hz, 1H), 4.91-4.99 (m, 1H), 4.17 (dt, J=13.2, 4.0 Hz, 2H), 3.48 (s, 1H), 3.38-3.43 (m, 1H), 2.59-2.71 (m, 2H), 2.18-2.25 (m, 1H), 1.77-1.83 (m, 1H), 1.48-1.58 (m, 1H), 1.22-1.33 (m, 1H), 1.08 (d, J=6.4 Hz, 3H) ppm. LRMS m/z (M+H) 273.1 found, 273.3 required.

Step 4: (2-(2H-1,2,3-triazol-2-yl)phenyl)((2R,5R)-5-((4-(2,2-difluoroethoxy)pyridin-2-yl)oxy)-2-methylpiperidin-1-yl)methanone A solution of 4-(2,2-difluoroethoxy)-2-(((3R,6R)-6-methylpiperidin-3-yl)oxy)pyridine (33 mg, 0.11 mmol), 2-(2H-1,2,3-triazol-2-yl)benzoic acid (20 mg, 0.11 mmol), HOBT (1.6 mg, 0.011 mmol), and EDC (30 mg, 0.16 mmol) in DMF (1.1 ml) was treated with triethylamine (37 μL, 0.26 mmol) and heated at 50° C. overnight. Additional 2-(2H-1,2,3-triazol-2-yl)benzoic acid (1.3 equiv.), EDC (1 equiv.), and triethylamine (1 equiv.) were added and heating continued overnight. The reaction was diluted with saturated, aqu. NaHCO$_3$ and extra water, then extracted 2× with EtOAc. The combined organics were washed with brine, dried over Na$_2$SO$_4$, filtered, and concentrated. The crude material was purified by silica gel gradient chromatography (0-40% EtOAc in hexanes), then further purified by reverse phase HPLC, providing the titled compound as a tacky solid. HRMS m/z (M+H) 444.1827 found, 444.1842 required.

TABLE 3

The following compounds were prepared using the foregoing methodology and general procedure described in Example 27, but substituting the appropriate carboxylic acid for 2-(2H-1,2,3-triazol-2-yl) benzoic acid, and substituting the appropriate alcohol for 2,2-difluoroethanol (Method A) or the appropriate alkyl halide for 1,1,-fifluoro-2-iodoethane (Method B), as described in the foregoing Reaction Schemes and Examples. The requisite starting materials were commercially available, described in the literature or readily synthesized by one skilled in the art of organic synthesis from commercially available reagents using conventional reactions without undue experimentation.

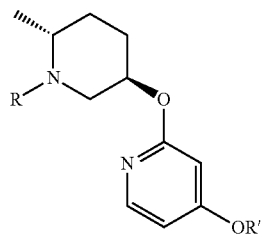

| Example | R | R' | Name | LRMS or HRMS (M + H⁺) |
|---|---|---|---|---|
| 28 | 2-(1H-1,2,3-triazol-2-yl)phenyl carbonyl | CH₂CF₃ | (2-(2H-1,2,3-triazol-2-yl)phenyl)((2R,5R)-2-methyl-5-((4-(2,2,2-trifluoroethoxy)pyridin-2-yl)oxy)piperidin-1-yl)methanone | Calc'd 462.1748, found 462.1732 |
| 29 | 2-(2H-tetrazol-2-yl)phenyl carbonyl | CH₂CHF₂ | 4-(2,2-difluoroethoxy)-2-{[(3R,6R)-6-methyl-1-{[2-(2H-tetrazol-2-yl)phenyl]carbonyl}piperidin-3-yl]oxy}pyridine | Calc'd 445.1797, found 445.1794 |
| 30 | 2-(2H-tetrazol-2-yl)phenyl carbonyl | CH₂CF₃ | 2-{[(3R,6R)-6-methyl-1-{[2-(2H-tetrazol-2-yl)phenyl]carbonyl}piperidin-3-yl]oxy}-4-(2,2,2-trifluoroethoxy)pyridine | Calc'd 463.1703, found 463.1683 |
| 31 | 2-[(methylsulfonyl)methyl]phenyl carbonyl | CH₂CHF₂ | 4-(2,2-difluoroethoxy)-2-{[(3R,6R)-6-methyl-1-({2-[(methylsulfonyl)methyl]phenyl}carbonyl)piperidin-3-yl]oxy}pyridine | Calc'd 469.2, found 469.1 |
| 32 | 2-(1-cyanocyclopropyl)phenyl carbonyl | CH₂CHF₂ | 1-(2-{[(2R,5R)-5-{[4-(2,2-difluoroethoxy)pyridin-2-yl]oxy}-2-methylpiperidin-1-yl]carbonyl}phenyl)cyclopropanecarbonitrile | Calc'd 442.2, found 442.1 |

TABLE 3-continued

The following compounds were prepared using the foregoing methodology and general procedure described in Example 27, but substituting the appropriate carboxylic acid for 2-(2H-1,2,3-triazol-2-yl) benzoic acid, and substituting the appropriate alcohol for 2,2-difluoroethanol (Method A) or the appropriate alkyl halide for 1,1,-fifluoro-2-iodoethane (Method B), as described in the foregoing Reaction Schemes and Examples. The requisite starting materials were commercially available, described in the literature or readily synthesized by one skilled in the art of organic synthesis from commercially available reagents using conventional reactions without undue experimentation.

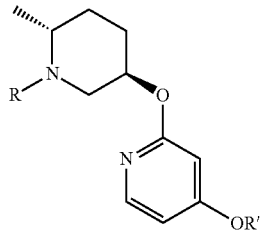

| Example | R | R' | Name | LRMS or HRMS (M + H⁺) |
|---|---|---|---|---|
| 33 | (3-(2H-1,2,3-triazol-2-yl)pyridin-2-yl)carbonyl | $CH_2CHF_2$ | 2-{[(2R,5R)-5-{[4-(2,2-difluoroethoxy)pyridin-2-yl]oxy}-2-methylpiperidin-1-yl]carbonyl}-3-(2H-1,2,3-triazol-2-yl)pyridine | Calc'd 445.2, found 445.2 |
| 34 | (3-fluoro-2-(2H-1,2,3-triazol-2-yl)phenyl)carbonyl | $CH_2CHF_2$ | 4-(2,2-difluoroethoxy)-2-{[(3R,6R)-1-{[3-fluoro-2-(2H-1,2,3-triazol-2-yl)phenyl]carbonyl}-6-methylpiperidin-3-yl]oxy}pyridine | Calc'd 462.2, found 462.4 |
| 35 | (4-fluoro-2-(2H-1,2,3-triazol-2-yl)phenyl)carbonyl | $CH_2CHF_2$ | 4-(2,2-difluoroethoxy)-2-{[(3R,6R)-1-{[4-fluoro-2-(2H-1,2,3-triazol-2-yl)phenyl]carbonyl}-6-methylpiperidin-3-yl]oxy}pyridine | Calc'd 462.2, found 462.2 |
| 36 | (2-fluoro-6-(2H-1,2,3-triazol-2-yl)phenyl)carbonyl | $CH_2CHF_2$ | 4-(2,2-difluoroethoxy)-2-{[(3R,6R)-1-{[2-fluoro-6-(2H-1,2,3-triazol-2-yl)phenyl]carbonyl}-6-methylpiperidin-3-yl]oxy}pyridine | Calc'd 462.2, found 462.3 |

TABLE 3-continued

The following compounds were prepared using the foregoing methodology and general procedure described in Example 27, but substituting the appropriate carboxylic acid for 2-(2H-1,2,3-triazol-2-yl) benzoic acid, and substituting the appropriate alcohol for 2,2-difluoroethanol (Method A) or the appropriate alkyl halide for 1,1,-fifluoro-2-iodoethane (Method B), as described in the foregoing Reaction Schemes and Examples. The requisite starting materials were commercially available, described in the literature or readily synthesized by one skilled in the art of organic synthesis from commercially available reagents using conventional reactions without undue experimentation.

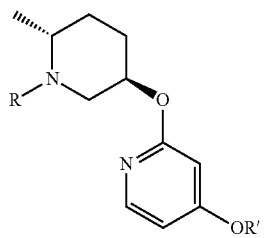

| Example | R | R' | Name | LRMS or HRMS (M + H$^+$) |
|---|---|---|---|---|
| 37 | (2-(3-methyl-1,2,4-oxadiazol-5-yl)phenyl)carbonyl | CH$_2$CHF$_2$ | 4-(2,2-difluoroethoxy)-2-{[(3R,6R)-6-methyl-1-{[2-(3-methyl-1,2,4-oxadiazol-5-yl)phenyl]carbonyl}piperidin-3-yl]oxy}pyridine | Calc'd 459.2, found 459.4 |
| 38 | (2-(5-methyl-1,2,4-oxadiazol-3-yl)phenyl)carbonyl | CH$_2$CHF$_2$ | 4-(2,2-difluoroethoxy)-2-{[(3R,6R)-6-methyl-1-{[2-(5-methyl-1,2,4-oxadiazol-3-yl)phenyl]carbonyl}piperidin-3-yl]oxy}pyridine | Calc'd 459.2, found 459.4 |

EXAMPLE 39

2-{[(3R,6R)-6-Methyl-1-{[2-(2H-1,2,3-triazol-2-yl)phenyl]carbonyl}piperidin-3-yl]oxy}pyridin-4-ol A solution of 4-(benzyloxy)-2-{[(3R,6R)-6-methyl-1-{[2-(2H-1,2,3-triazol-2-yl)phenyl]carbonyl}piperidin-3-yl]oxy}pyridine (Example 6, 0.220 g, 0.469 mmol) and palladium (10 wt % on activated carbon, 5.0 mg) in degassed methanol (5 mL) was stirred for 3.5 hours under an atmosphere of hydrogen gas. The degassed mixture was then filtered over celite, washing with EtOH. The filtrate was concentrated to give the crude title compound which was used without further purification. HRMS m/z (M+H) 380.1723 found, 380.1717 required.

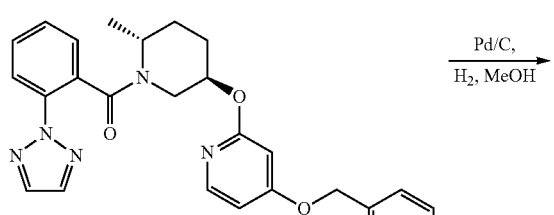

EXAMPLE 40

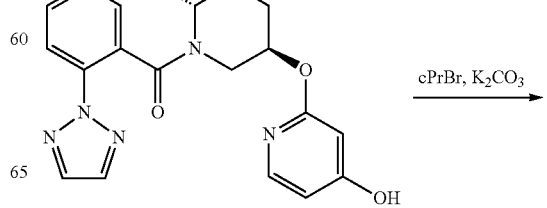

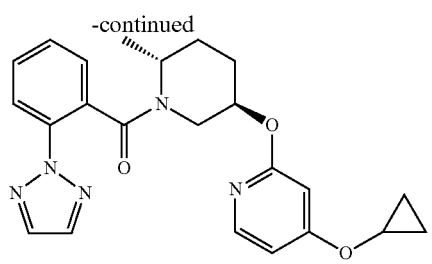

4-(Cyclopropyloxy)-2-{[(3R,6R)-6-methyl-1-{[2-(2H-1,2,3-triazol-2-yl)phenyl]carbonyl}-piperidin-3-yl]oxy}pyridine

A solution of 2-{[(3R,6R)-6-methyl-1-{[2-(2H-1,2,3-triazol-2-yl)phenyl]carbonyl}piperidin-3-yl]oxy}pyridin-4-ol (Example 39, 0.012 g, 0.032 mmol), cyclopropyl bromide (5.7 mg, 0.047 mmol), and potassium carbonate (5.7 mg, 0.041 mmol) in DMF (1 mL) was heated to 40° C. overnight. Additional cyclopropyl bromide (5.7 mg, 0.047 mmol) was added, and the mixture was heated at 40° C. for 72 h, then filtered and purified by reverse phase HPLC, providing the title compound. HRMS m/z (M+H) 420.2033 found, 420.3032 required.

EXAMPLE 44

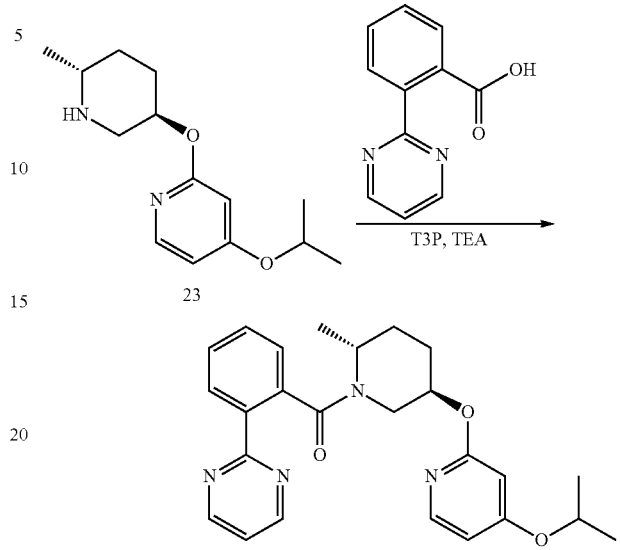

TABLE 4

The following compounds were prepared using the foregoing methodology and general procedure described in Example 40, but substituting the appropriate alkyl halide for cyclopropyl bromide, as described in the foregoing Reaction Schemes and Examples. The requisite starting materials were commercially available, described in the literature or readily synthesized by one skilled in the art of organic synthesis from commercially available reagents using conventional reactions without undue experimentation.

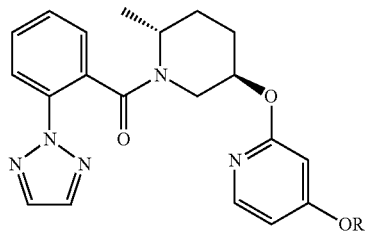

| Example | R | Name | LRMS or HRMS (M + H+) |
|---|---|---|---|
| 41 | (oxetan-3-yl) | 2-{[(3R,6R)-6-methyl-1-{[2-(2H-1,2,3-triazol-2-yl)phenyl]carbonyl}piperidin-3-yl]oxy}-4-(oxetan-3-yloxy)pyridine | Calc'd 436.1981, found 436.1986 |
| 42 | isobutyl | 4-(2-methylpropoxy)-2-{[(3R,6R)-6-methyl-1-{[2-(2H-1,2,3-triazol-2-yl)phenyl]carbonyl}piperidin-3-yl]oxy}pyridine | Calc'd 436.2345, found 436.2350 |
| 43 | propyl | 2-{[(3R,6R)-6-methyl-1-{[2-(2H-1,2,3-triazol-2-yl)phenyl]carbonyl}piperidin-3-yl]oxy}-4-propoxypyridine | Calc'd 422.2188, found 422.2189 |

2-(2-{[(2R,5R)-2-Methyl-5-{[4-(1-methylethoxy)pyridin-2-yl]oxy}piperidin-1-yl]carbonyl}phenyl)pyrimidine

Step 1: 4-Isopropoxy-2-(((3R,6R)-6-methylpiperidin-3-yl)oxy)pyridine (23)

The title compound was prepared by the procedure described for the synthesis of 4-methoxy-2-(((3R,6R)-6-methylpiperidin-3-yl)oxy)pyridine (Example 6, 12), substituting 4-isopropoxypyridin-2-ol for 4-methoxypyridin-2-ol. HRMS m/z (M+H) 433.2234 found, 433.2236 required.

Step 2: 2-(2-{[(2R,5R)-2-Methyl-5-{[4-(1-methylethoxy)pyridin-2-yl]oxy}piperidin-1-yl]carbonyl}phenyl)pyrimidine A solution of 4-isopropoxy-2-(((3R,6R)-6-methylpiperidin-3-yl)oxy)pyridine hydrogen chloride (0.010 g, 0.036 mmol), 2-(pyrimidin-2-yl)benzoic acid (8.0 mg, 0.040 mmol), and triethylamine (0.013 mL, 0.091 mmol) in DMF (0.3 mL) was treated with 2,4,6-tripropyl-1,3,5,2,4,6-trioxatriphosphorinane-2,4,6-trioxide (T3P, 50% in EtOAc, 0.043 mL, 0.073 mmol) and stirred at RT overnight. Additional 2,4,6-tripropyl-1,3,5,2,4,6-trioxatriphosphorinane-2,4,6-trioxide (T3P, 50% in EtOAc, 0.043 mL, 0.073 mmol) was added, and the reaction was heated at 50° C. for 2.5 hours, filtered, and purified by reverse phase preparatory HPLC, providing the title compound. HRMS m/z (M+H) 433.2234 found, 433.2236 required.

TABLE 5

The following compounds were prepared using the foregoing methodology and general procedure described in Example 44, but substituting the appropriate piperidine and pyrimidine carboxylic acid (or potassium carboxylate), as described in the foregoing Reaction Schemes and Examples. The requisite starting materials were commercially available, described in the literature or readily synthesized by one skilled in the art of organic synthesis from commercially available reagents using conventional reactions without undue experimentation.

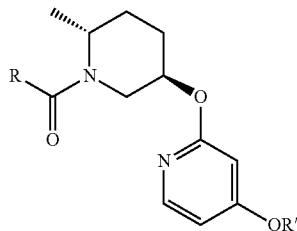

| Example | R | R' | Name | LRMS or HRMS (M + H+) |
|---|---|---|---|---|
| 45 | (2-pyrimidin-2-yl-phenyl)carbonyl | CH₂CHF₂ | 2-(2-{[(2R,5R)-5-{[4-(2,2-difluoroethoxy)pyridin-2-yl]oxy}-2-methylpiperidin-1-yl]carbonyl}phenyl)pyrimidine | Calc'd 455.1889, found 455.1872 |
| 46 | (4-fluoro-2-pyrimidin-2-yl-phenyl)carbonyl | CH₂CHF₂ | 2-(2-{[(2R,5R)-5-{[4-(2,2-difluoroethoxy)pyridin-2-yl]oxy}-2-methylpiperidin-1-yl]carbonyl}-5-fluorophenyl)pyrimidine | Calc'd 473.2, found 473.4 |
| 47 | (3-pyrimidin-2-yl-pyridin-2-yl)carbonyl | CH₂CHF₂ | 2-(2-{[(2R,5R)-5-{[4-(2,2-difluoroethoxy)pyridin-2-yl]oxy}-2-methylpiperidin-1-yl]carbonyl}pyridin-3-yl)pyrimidine | Calc'd 456.2, found 456.3 |

EXAMPLE 48

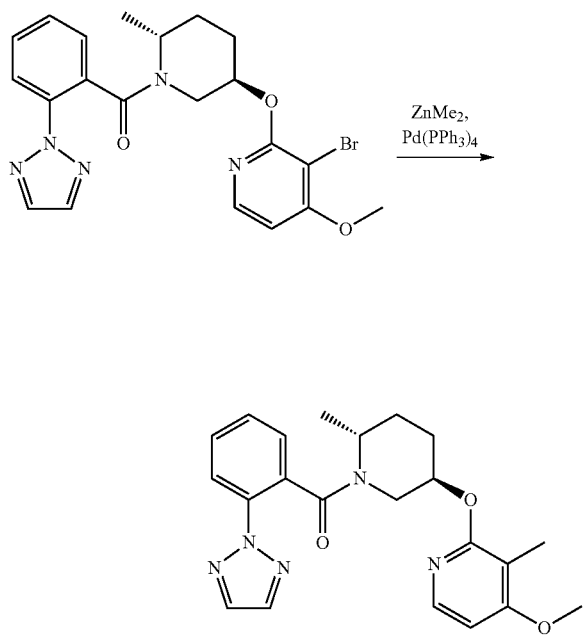 [SMILES: COc1ccnc(O[C@@H]2CC[C@@H](C)N(C(=O)c3ccccc3-n3nccn3)C2)c1Br ; COc1ccnc(O[C@@H]2CC[C@@H](C)N(C(=O)c3ccccc3-n3nccn3)C2)c1C]

4-Methoxy-3-methyl-2-{[(3R,6R)-6-methyl-1-{[2-(2H-1,2,3-triazol-2-yl)phenyl]carbonyl}piperidin-3-yl]oxy}pyridine A solution of 3-bromo-4-methoxy-2-{[(3R,6R)-6-methyl-1-{[2-(2H-1,2,3-triazol-2-yl)phenyl]carbonyl}piperidin-3-yl]oxy}pyridine (Example 4, 0.020 g, 0.042 mmol) in THF (1 mL) under an atmosphere of nitrogen was treated with dimethylzinc (1.0 M in THF, 0.085 mL, 0.085 mmol) and tetrakis(triphenylphosphine)palladium(0) (4.9 mg, 0.0042 mmol) and heated to 80° C. for 4 h. Additional dimethylzinc (1.0 M in THF, 0.085 mL, 0.085 mmol) and tetrakis(triphenylphosphine)palladium(0) (4.9 mg, 0.0042 mmol) were added, and the mixture was heated to 100° C. overnight. The reaction was quenched with saturated aqueous ammonium chloride, stirred with Quadrapure™ for 30 min, filtered, and purified by reverse phase preparatory HPLC, providing the title compound. HRMS m/z (M+H) 408.2036 found, 408.2030 required.

EXAMPLE 49

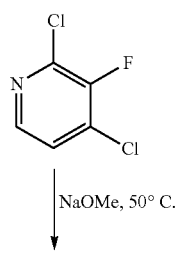

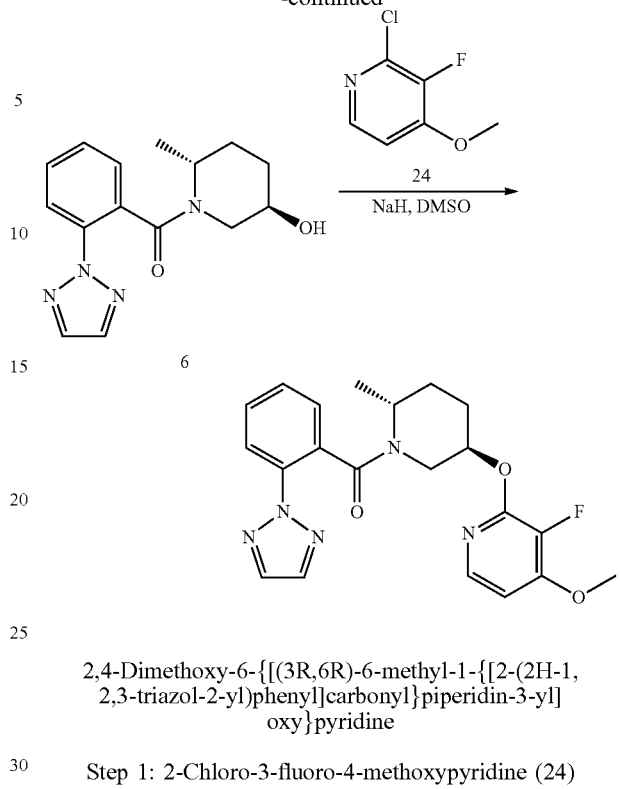

2,4-Dimethoxy-6-{[(3R,6R)-6-methyl-1-{[2-(2H-1,2,3-triazol-2-yl)phenyl]carbonyl}piperidin-3-yl]oxy}pyridine Step 1: 2-Chloro-3-fluoro-4-methoxypyridine (24)

A solution of 2,4-dichloro-3-fluoropyridine (0.200 g, 1.20 mmol) in DMF (2.4 mL) was treated with sodium methoxide (0.072 g, 1.3 mmol) and heated at 50° C. overnight. The mixture was quenched with saturated aqueous ammonium chloride, diluted with water, and extracted 3× with ethyl acetate. The combined organic fractions were washed with brine, dried over sodium sulfate, filtered, and concentrated. The residue was purified by silica gel gradient chromatography (0-20% ethyl acetate in hexanes), providing the title compound as a white solid. LRMS m/z (M+H) 162.1 found, 162.0 required.

Step 2: 3-Fluoro-4-methoxy-2-{[(3R,6R)-6-methyl-1-{[2-(2H-1,2,3-triazol-2-yl)phenyl]carbonyl}piperidin-3-yl]oxy}pyridine The title compound was prepared by the procedure described for the synthesis of 4-ethoxy-2-{[(3R,6R)-6-methyl-1-{[2-(2H-1,2,3-triazol-2-yl)phenyl]carbonyl}piperidin-3-yl]oxy}pyridine (Example 1), substituting 2-chloro-3-fluoro-4-methoxypyridine for 2-chloro-4-ethoxypyridine. HRMS m/z (M+H) 412.1761 found, 412.1782 required.

EXAMPLE 50

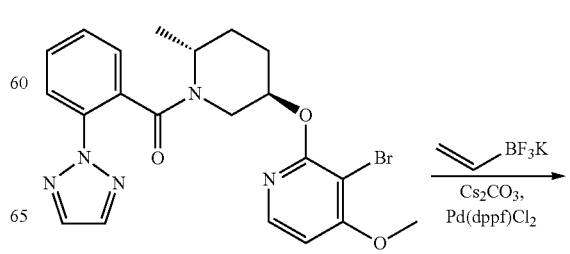

-continued

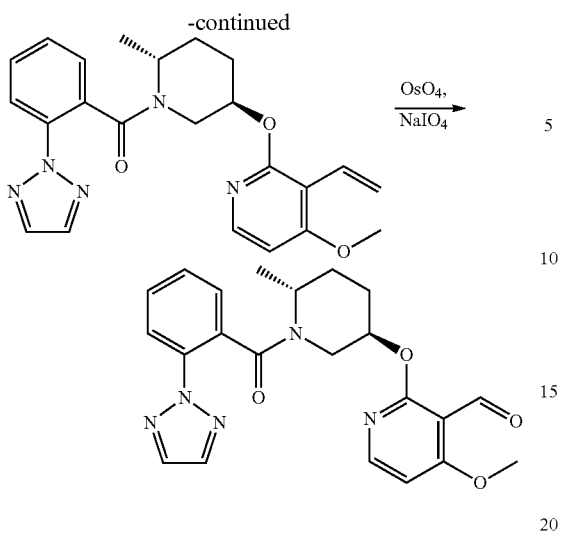

Step 1: 3-Ethenyl-4-methoxy-2-{[(3R,6R)-6-methyl-1-{[2-(2H-1,2,3-triazol-2-yl)phenyl]carbonyl}piperidin-3-yl]oxy}pyridine To a solution of 3-bromo-4-methoxy-2-{[(3R,6R)-6-methyl-1-{[2-(2H-1,2,3-triazol-2-yl)phenyl]carbonyl}piperidin-3-yl]oxy}pyridine (Example 4, 0.168 g, 0.356 mmol), potassium vinyltrifluoroborate (0.072 g, 0.53 mmol), and cesium carbonate (0.232 g, 0.711 mmol) in THF (1.8 mL) and water (0.2 mL) under an atmosphere of nitrogen was added [1,1'-bis(diphenylphosphino)ferrocene]dichloropalladium(II), complex with dichloromethane (0.026 g, 0.036 mmol). The reaction was sealed and stirred at 100° C. overnight, then diluted with ethyl acetate and washed with saturated aqueous sodium bicarbonate and brine, dried over sodium sulfate, filtered, and concentrated. The residue was purified by silica gel gradient chromatography (0-50% ethyl acetate in hexanes), providing the title compound as an orange oil. HRMS m/z (M+H) 420.2035 found, 420.2030 required.

Step 2: 4-Methoxy-2-{[(3R,6R)-6-methyl-1-{[2-(2H-1,2,3-triazol-2-yl)phenyl]carbonyl}piperidin-3-yl]oxy}pyridine-3-carbaldehyde To a solution of 3-ethenyl-4-methoxy-2-{[(3R,6R)-6-methyl-1-{[2-(2H-1,2,3-triazol-2-yl)phenyl]carbonyl}piperidin-3-yl]oxy}pyridine (0.090 g, 0.22 mmol) in a 2:1 mixture of THF:water (3 mL) was added sodium periodate (0.115 g, 0.536 mmol) followed by osmium tetroxide (2.5% by wt in water, 0.03 mL, 0.002 mmol). After 4 h, the reaction was partitioned between ethyl acetate and saturated aqueous sodium bicarbonate. The organic layer was washed with water and brine, dried over sodium sulfate, filtered, and concentrated. The residue was purified by reverse phase preparatory HPLC, providing the title compound. HRMS m/z (M+H) 422.1831 found, 422.1825 required.

TABLE 6

The following compound was prepared using the foregoing methodology and general procedure described in Example 50, but substituting the appropriate alkene for 3-ethenyl-4-methoxy-2-{[(3R,6R)-6-methyl-1-{[2-(2H-1,2,3-triazol-2-yl)phenyl]carbonyl}piperidin-3-yl]oxy}pyridine, as described in the foregoing Reaction Schemes and Examples. The requisite starting materials were commercially available, described in the literature or readily synthesized by one skilled in the art of organic synthesis from commercially available reagents using conventional reactions without undue experimentation.

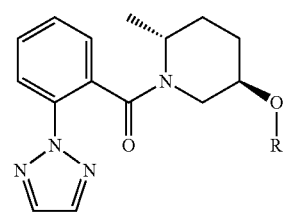

| Example | R | Name | LRMS or HRMS (M + H+) |
|---|---|---|---|
| 51 | 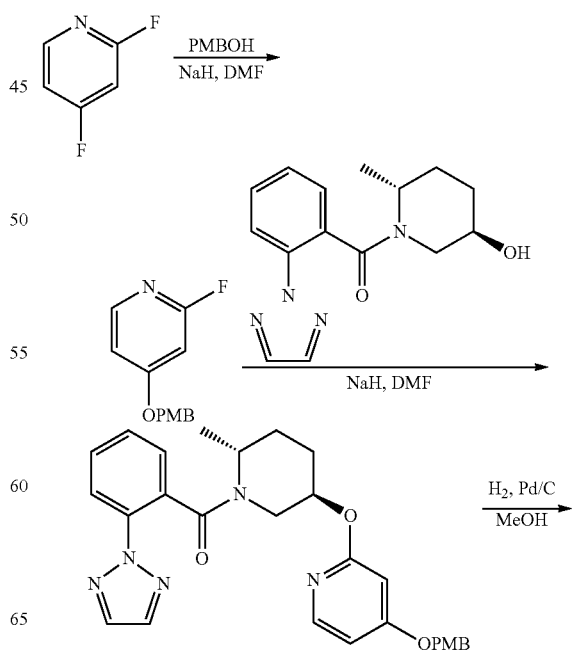 | 1-(4-methoxy-2-{[(3R,6R)-6-methyl-1-{[2-(2H-1,2,3-triazol-2-yl)phenyl]carbonyl}piperidin-3-yl]oxy}pyridin-3-yl)ethanone | Calc'd 436.1981, found 436.1979 |

EXAMPLE 52

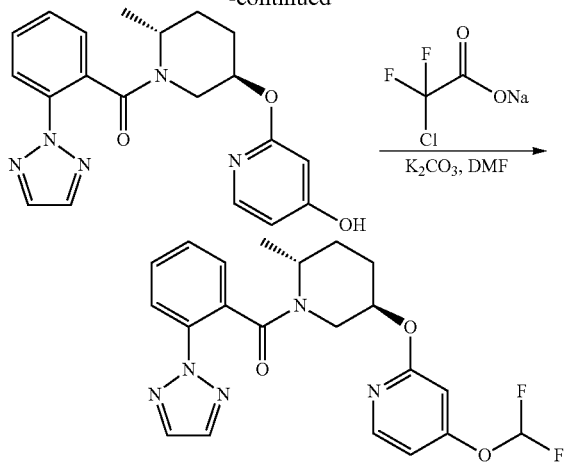

(2-(2H-1,2,3-Triazol-2-yl)phenyl)((2R,5R)-5-((4-(difluoromethoxy)pyridin-2-yl)oxy)-2-methylpiperidin-1-yl)methanone Step 1: 2-Fluoro-4-((4-methoxybenzyl)oxy)pyridine To a solution of para-methoxybenzyl alcohol (1.92 g, 13.9 mmol) in DMF (15 mL) was added sodium hydride (60% dispersion in mineral oil, 1.10 g, 27.5 mmol) at 0-5° C. in portions. After stirring for 15 min at RT, a solution of 2,4-difluoropyridine (2.00 g, 17.4 mmol) in DMF (5 mL) was added. The resulting mixture was stirred RT for 3 h. The mixture was quenched with saturated NH$_4$Cl and extracted 3× with EtOAc. The combined organic layers were washed with brine, dried over sodium sulfate, filtered and concentrated. The residue was purified by silica gel gradient chromatography (1:10 to 1:2 EtOAc in petroleum ether), providing the title compound as a white solid. LRMS m/z (M+H) 234.1 found, 234.1 required.

Step 2: (2-(2H-1,2,3-Triazol-2-yl)phenyl)((2R,5R)-5-((4-((4-methoxybenzyl)oxy)pyridin-2-yl)oxy)-2-methylpiperidin-1-yl)methanone To a solution of (2-(2H-1,2,3-triazol-2-yl)phenyl)((2R,5R)-5-hydroxy-2-methylpiperidin-1-yl)methanone (100 mg, 0.35 mmol) in DMF (3 mL) was added sodium hydride (60% dispersion in mineral oil, 42 mg, 1.05 mmol) at 0~5° C. The mixture was stirred at RT for 30 min, then 2-fluoro-4-((4-methoxybenzyl)oxy)pyridine (163 mg, 0.7 mmol) was added and the resulting mixture was stirred at RT overnight. The mixture was quenched with saturated and extracted 3× with EtOAc. The combined organic layers were washed with brine, dried over sodium sulfate, filtered, and concentrated. The residue was purified by silica gel gradient chromatography (1:10 to 1:3 EtOAc in petroleum ether), providing the title compound as yellow oil. LRMS m/z (M+H) 500.2 found, 500.2 required.

Step 3: (2-(2H-1,2,3-Triazol-2-yl)phenyl)((2R,5R)-5-((4-hydroxypyridin-2-yl)oxy)-2-methylpiperidin-1-yl)methanone A mixture of 2-(2H-1,2,3-triazol-2-yl)phenyl)((2R,5R)-5-((4-(4-methoxybenzyl)oxy)pyridin-2-yl)oxy)-2-methylpiperidin-1-yl)methanone (145 mg, 0.29 mmol) and palladium on carbon (10 wt %, 50 mg) in MeOH (10 mL) was stirred at RT under 1 atm of H$_2$ for 3 h. The mixture was filtered over celite and the filtrate was concentrated and dried to give the title compound as white solid, which was used in the next step without further purification. LRMS m/z (M+H) 380.2 found, 380.2 required Step 4: (2-(2H-1,2,3-Triazol-2-yl)phenyl)((2R,5R)-5-((4-(difluoromethoxy)pyridin-2-yl)oxy)-2-methyl-piperidin-1-yl)methanone To a solution of (2-(2H-1,2,3-triazol-2-yl)phenyl)((2R,5R)-5-((4-hydroxypyridin-2-yl)oxy)-2-methylpiperidin-1-yl)-methanone (50 mg, 0.132 mmol) in DMF (10 mL) was added potassium carbonate (456 mg, 3.3 mmol). After the mixture was stirred for 30 min, sodium 2-chloro-2,2-difluoroacetate (60.3 mg, 0.396 mmol) was added. The resulting mixture was stirred at 80° C. for 1.5 h. The reaction was cooled to RT and the mixture was quenched with water and extracted 3× with EtOAc. The combined organic layers were washed with brine, dried over sodium sulfate, filtered and concentrated. The residue was purified by prep-HPLC to give the title compound as white solid. LRMS m/z (M+H) 430.2 found, 430.2 required.

EXAMPLE 53

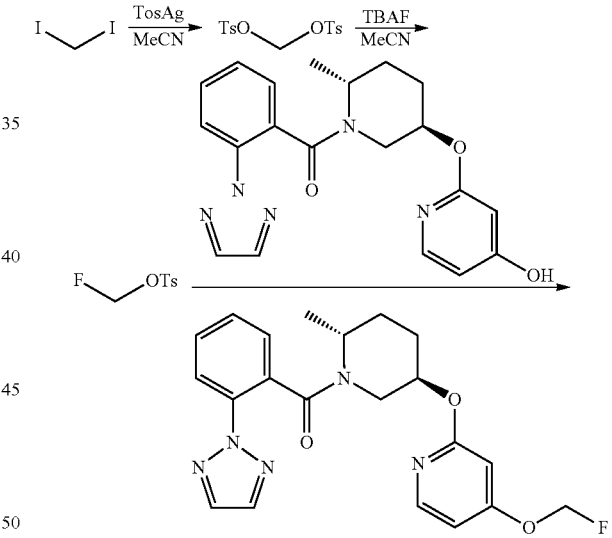

(2-(2H-1,2,3-Triazol-2-yl)phenyl)((2R,5R)-5-((4-(fluoromethoxy)pyridin-2-yl)oxy)-2-methylpiperidin-1-yl)methanone Step 1: Methylene bis(4-methylbenzenesulfonate)

A mixture of tosylsilver (3 g, 10.7 mmol) and diiodomethane (1.43 g, 4.43 mmol) in acetonitrile (30 mL) was refluxed under nitrogen atmosphere overnight. The mixture was cooled to RT and then filtered. The filtrate was concentrated and the solid was dissolved dichloromethane (50 mL). The resulting mixture was filtered and the filtrate was concentrated in vacuo to give the title compound as white solid, which was used in the next step directly.

Step 2: Fluoromethyl 4-methylbenzenesulfonate

A mixture of methylene bis(4-methylbenzenesulfonate) (1.6 g, 4.48 mmol) and TBAF (1.15 g, 4.48 mmol) in acetonitrile (15 mL) was heated at 80° C. overnight. The mixture was cooled to RT and concentrated in vacuo. The residue was purified by silica gel gradient chromatography (1:5 EtOAc in petroleum ether), providing the title compound as a colorless oil.

Step 3: (2-(2H-1,2,3-Triazol-2-yl)phenyl)((2R,5R)-5-((4-(fluoromethoxy)pyridin-2-yl)oxy)-2-methylpiperidin-1-yl)methanone A mixture of fluoromethyl 4-methylbenzenesulfonate (55 mg, 0.27 mmol), (2-(2H-1,2,3-triazol-2-yl)phenyl)((2R,5R)-5-(4-hydroxypyridin-2-yl)oxy)-2-methylpiperidin-1-yl)methanone (85 mg, 0.22 mmol), and potassium carbonate (62 mg, 0.45 mmol) in acetone (20 mL) was heated at reflux overnight. The mixture was cooled to RT and concentrated in vacuo. The residue was extracted with dichloromethane/water and the organic layer was washed with brine, dried over sodium sulfate, filtered, and concentrated. The residue was purified by prep-HPLC to give the title compound as white solid. LRMS m/z (M+H) 412.2 found, 412.2 required.

EXAMPLE 54

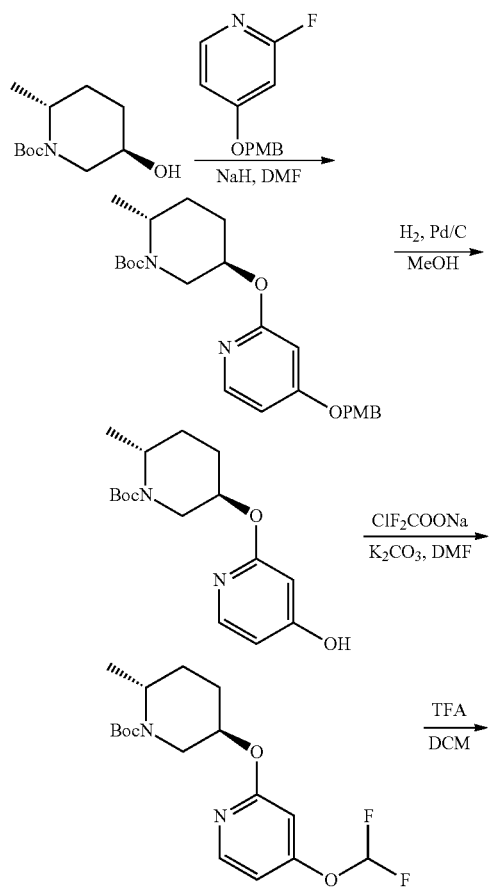

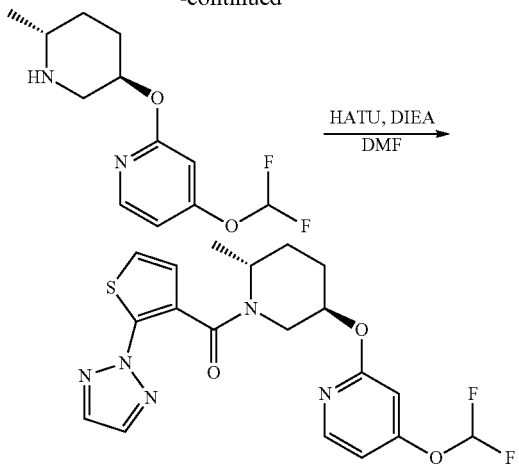

(2-(2H-1,2,3-Triazol-2-yl)thiophen-3-yl)((2R,5R)-5-((4-(difluoromethoxy)pyridin-2-yl)oxy)-2-methylpiperidin-1-yl)methanone

Step 1: (2R,5R)-tert-Butyl 5-((4-((4-methoxybenzyl)oxy)pyridin-2-yl)oxy)-2-methylpiperidine-1-carboxylate To a solution of (2R,5R)-tert-butyl 5-hydroxy-2-methylpiperidine-1-carboxylate (500 mg, 2.32 mmol) in DMF (10 mL) was added sodium hydride (60% dispersion in mineral oil, 278 mg, 6.95 mmol) at 0° C. The mixture was stirred at RT for 30 min and cooled to 0° C., then 2-fluoro-4-((4-methoxybenzyl)oxy)pyridine (1080 mg, 4.63 mmol) was added. The resulting mixture was warmed to RT and stirred for 4 h. The mixture was quenched with saturated NH$_4$Cl and extracted with EtOAc. The combined organic layers were washed with brine, dried over sodium sulfate, filtered, and concentrate. The residue was purified by silica gel gradient chromatography (1:5 EtOAc in petroleum ether), providing the title compound as light yellow oil. LRMS m/z (M+H) 429.1 found, 429.1 required.

Step 2: (2R,5R)-tert-Butyl 5-((4-hydroxypyridin-2-yl)oxy)-2-methylpiperidine-1-carboxylate A mixture of (2R,5R)-tert-butyl-5-((4-((4-methoxybenzyl)oxy)pyridin-2-yl)oxy)-2-methylpiperidine-1-carboxylate (550 mg, 1.28 mmol) and palladium on carbon (10 wt %, 100 mg) in methanol (15 mL) was stirred at room temperature under a hydrogen atmosphere for 1.5 h. The mixture was filtered and the filtrate was concentrated in vacuo to give the title compound as a colorless oil, which was used in the next step directly. LRMS m/z (M+H) 309.2 found, 309.2 required.

Step 3: (2R,5R)-tert-Butyl 5-((4-(difluoromethoxy)pyridin-2-yl)oxy)-2-methylpiperidine-1-carboxylate A mixture of (2R,5R)-tert-butyl 5-((4-hydroxypyridin-2-yl)oxy)-2-methylpiperidine-1-carboxylate (380 mg, 1.23 mmol), sodium 2-chloro-2,2-difluoroacetate (375 mg, 2.47 mmol), and potassium carbonate (1.7 g, 12.3 mmol) in DMF (20 mL) was stirred at 80° C. overnight. The reaction was cooled to RT, quenched with water, and extracted with EtOAc. The combined organic layers were washed with brine, dried over sodium sulfate, filtered, and concentrated. The residue was purified by silica gel gradient chromatography (1:5 EtOAc in petroleum ether), providing the title compound as a colorless oil. LRMS m/z (M+H) 359.1 found, 359.1 required.

Step 4: 4-(Difluoromethoxy)-2-(((3R,6R)-6-methyl-piperidin-3-yl)oxy)pyridine

To a solution of (2R,5R)-tert-butyl 5-((4-(difluoromethoxy)pyridin-2-yl)oxy)-2-methylpiperidine-1-carboxylate (205 mg, 0.573 mmol) in dichloromethane (10 mL) was added trifluoroacetic acid (5 mL) at 0° C. The mixture was allowed to heat to RT and stirred for 3 h. The mixture was concentrated in vacuo to give the title compound as an oil, which was used in the next step directly. LRMS m/z (M+H) 259.2 found, 259.2 required.

Step 5: (2-(2H-1,2,3-Triazol-2-yl)thiophen-3-yl)((2R,5R)-5-((4-(difluoromethoxy)pyridin-2-yl)oxy)-2-methylpiperidin-1-yl)methanone A mixture of 4-(difluoromethoxy)-2-(((3R,6R)-6-methyl-piperidin-3-yl)oxy)pyridine (50 mg, 0.134 mmol), DIPEA (135 mg, 1.05 mmol), HATU (76.5 mmol, 0.2 mmol), and 2-(2H-1,2,3-triazol-2-yl)thiophene-3-carboxylic acid (30 mg, 0.154 mmol) in DMF (2 mL) was stirred at room temperature overnight. The mixture was filtered and purified by prep-HPLC to give the title compound as a white solid. LRMS m/z (M+H) 436.1 found, 436.1 required.

TABLE 7

The following compound was prepared using the foregoing methodology and general procedure described in Example 54, but substituting the appropriate acid for 2-(2H-1,2,3-triazol-2-yl)thiophene-3-carboxylic acid, as described in the foregoing Reaction Schemes and Examples. The requisite starting materials were commercially available, described in the literature or readily synthesized by one skilled in the art of organic synthesis from commercially available reagents using conventional reactions without undue experimentation.

| Example | R | Name | LRMS (M + H⁺) |
|---|---|---|---|
| 55 | | 4-(difluoromethoxy)-2-{[(3R,6R)-6-methyl-1-{[4-(2H-1,2,3-triazol-2-yl)thiophen-3-yl]carbonyl}piperidin-3-yl]oxy}pyridine | Calc'd 436.1, found 436.1 |
| 56 | | 1-(2-{[(2R,5R)-5-{[4-(difluoromethoxy)pyridin-2-yl]oxy}-2-methylpiperidin-1-yl]carbonyl}phenyl)cyclopropanecarbonitrile | Calc'd 428.1, found 428.1 |

TABLE 7-continued

| | | | |
|---|---|---|---|
| 57 | | 4-(difluoromethoxy)-2-{[(3R,6R)-6-methyl-1-{[2-(2H-tetrazol-2-yl)phenyl]carbonyl}piperidin-3-yl]oxy}pyridine | Calc'd 431.2, found 431.1 |

EXAMPLE 58

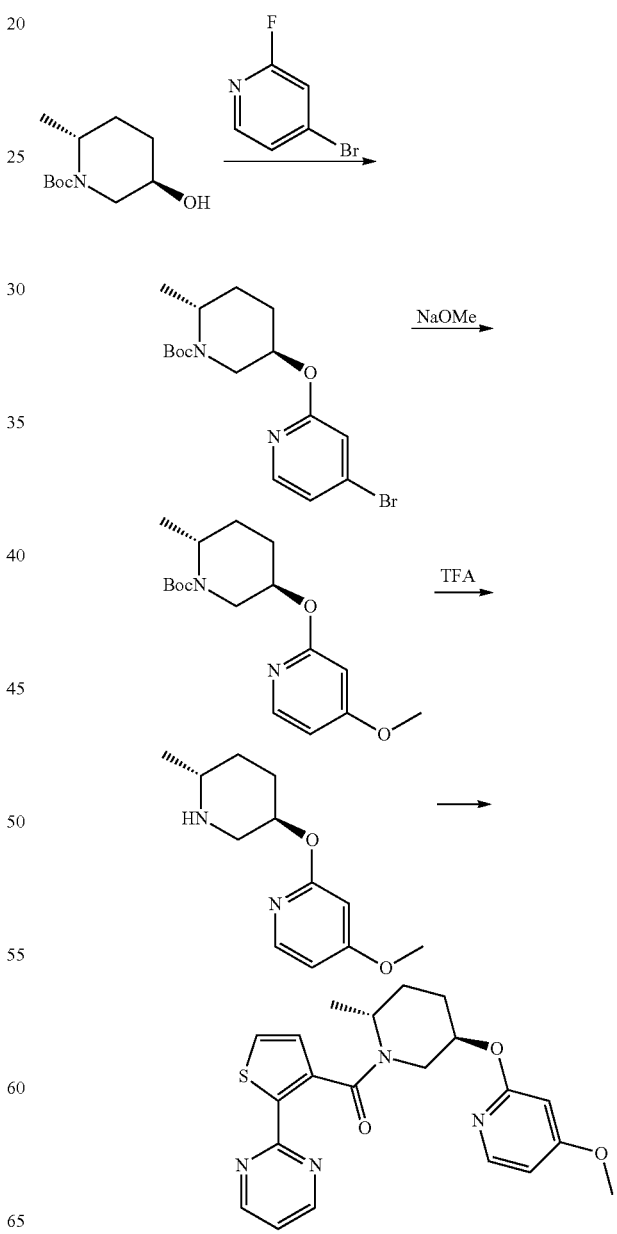

((2R,5R)-5-((4-Methoxypyridin-2-yl)oxy)-2-methyl-piperidin-1-yl)(2-(pyrimidin-2-yl)thiophen-3-yl)methanone Step 1: (2R,5R)-tert-Butyl 5-((4-bromopyridin-2-yl)oxy)-2-methylpiperidine-1-carboxylate To a solution of (2R,5R)-tert-butyl 5-hydroxy-2-methylpiperidine-1-carboxylate (200 mg, 0.93 mmol) in DMF (2.0 mL) was added sodium hydride (60% dispersion in mineral oil, 74 mg, 1.9 mmol) at 0° C. After the mixture was stirred at 0° C. for 0.5 h, a solution of 4-bromo-2-fluoropyridine (92 mg, 0.53 mmol) in DMF (0.5 ml) was added. The resulting mixture was allowed to warm to RT and stirred for 4 h, then poured into water and extracted 3× with EtOAc. The combined organic layers were washed with brine, dried over magnesium sulfate, and concentrated. The combined organic layers were washed with brine, dried over sodium sulfate, filtered, and concentrated. The residue was purified by silica gel gradient chromatography (1:5 EtOAc in petroleum ether), providing the title compound as a pale yellow oil. LRMS m/z (M+H) 371.1, 373.1 found, 371.1, 373.1 required.

Step 2: (2R,5R)-tert-Butyl 5-((4-methoxypyridin-2-yl)oxy)-2-methylpiperidine-1-carboxylate To a solution of (2R,5R)-tert-butyl 5-((4-bromopyridin-2-yl)oxy)-2-methylpiperidine-1-carboxylate (300 mg, 0.81 mmol) in methanol (3 ml) was added sodium methanolate (87 mg, 1.62 mmol). The mixture was stirred at 70° C. overnight. After cooling to RT, the mixture was concentrated in vacuo. The combined organic layers were washed with brine, dried over sodium sulfate, filtered, and concentrated. The residue was purified by silica gel gradient chromatography (1:5 EtOAc in petroleum ether), providing the title compound as a pale yellow oil. LRMS m/z (M+H) 323.1 found, 323.1 required.

Step 3: 4-Methoxy-2-(((3R,6R)-6-methylpiperidin-3-yl)oxy)pyridine

A solution of (2R,5R)-tert-butyl 5-((4-methoxypyridin-2-yl)oxy)-2-methylpiperidine-1-carboxylate (100 mg, 0.31 mmol) in trifluoroacetic acid (1 mL) and dichloromethane (1 mL) was stirred at RT for 0.5 h, then concentrated in vacuo to give the title compound as a yellow oil, which was used directly without any further purification. LRMS m/z (M+H) 223.1 found, 223.1 required.

Step 4: ((2R,5R)-5-((4-Methoxypyridin-2-yl)oxy)-2-methylpiperidin-1-yl)(2-(pyrimidin-2-yl)thiophen-3-yl)methanone A solution of 4-methoxy-2-(((3R,6R)-6-methylpiperidin-3-yl)oxy)pyridine (100 mg, 0.45 mmol), HATU (342 mg, 0.90 mmol), DIPEA (173 mg, 1.35 mmol), and 2-(pyrimidin-2-yl)thiophen-3-carboxylic acid (85 mg, 0.37 mmol) in dichloromethane (3 mL) was stirred at RT for 9 h. The mixture was poured into water and extracted 3× with EtOAc. The combined organic layers were washed with brine, dried over magnesium sulfate, filtered, and concentrated. The residue was purified by prep-HPLC to give the title compound as a white solid. LRMS m/z (M+H) 411.1 found, 411.1 required.

TABLE 8

The following compound was prepared using the foregoing methodology and general procedure described in Example 58, but substituting the appropriate acid for 2-(pyrimidin-2-yl)thiophene-3-carboxylic acid, as described in the foregoing Reaction Schemes and Examples. The requisite starting materials were commercially available, described in the literature or readily synthesized by one skilled in the art of organic synthesis from commercially available reagents using conventional reactions without undue experimentation.

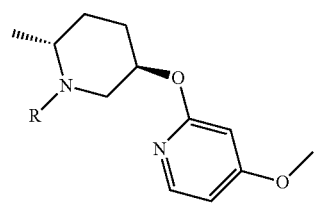

| Example | R | Name | LRMS (M + H⁺) |
|---|---|---|---|
| 59 | 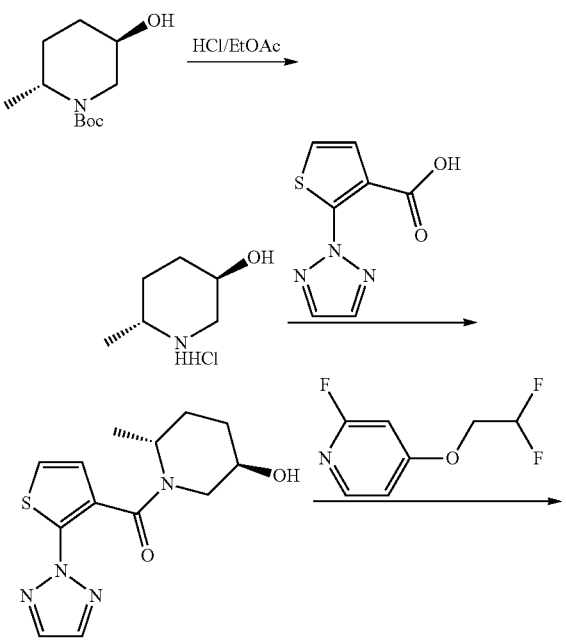 | 4-methoxy-2-{[(3R,6R)-6-methyl-1-{[2-(2H-1,2,3-triazol-2-yl)thiophen-3-yl]carbonyl}piperidin-3-yl]oxy}pyridine | Calc'd 400.1, found 400.1 |

EXAMPLE 60

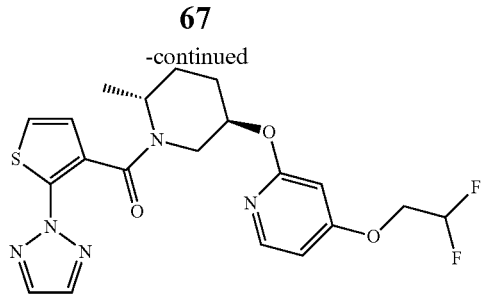

(2-(2H-1,2,3-Triazol-2-yl)thiophen-3-yl)((2R,5R)-5-((4-(2,2-difluoroethoxy)pyridin-2-yl)oxy)-2-methyl-piperidin-1-yl)methanone Step 1: (3R,6R)-6-Methylpiperidin-3-ol (13)

To a solution of (2R,5R)-tert-butyl 5-hydroxy-2-methyl-piperidine-1-carboxylate (1.0 g, 4.65 mmol) in EtOAc (10 mL) was added HCl in EtOAc (4 M, 20 mL) at 0° C. The reaction was warmed to RT and stirred for 4 h. The mixture was concentrated in vacuo to give the title compound which was used without further purification. LRMS m/z (M+H) 116.1 found, 116.1 required.

Step 2: (2-(2H-1,2,3-Triazol-2-yl)thiophen-3-yl)((2R,5R)-5-hydroxy-2-methylpiperidin-1-yl)methanone To a solution of 2-(2H-1,2,3-triazol-2-yl)thiophene-3-carboxylic acid (1.0 g, 5.12 mmol) in SOCl$_2$ (10 mL) was stirred at 80° C. for 0.5 h. After cooling to RT, the mixture was concentrated in vacuo. The residue was dissolved in dichloromethane (15 mL) and the resulting solution was dropwise added to a solution of DIPEA (360 mg, 23.6 mmol) and (3R,6R)-6-methylpiperidin-3-ol (800 mg, 4.65 mmol) in dichloromethane (10 mL) at 0° C. The resulting mixture was stirred at RT for 9 h, quenched with water (20 mL), and extracted 3× with dichloromethane. The combined organic layers were dried over magnesium sulfate, filtered, and concentrated. The residue was purified by prep-TLC (1:1 EtOAc in petroleum ether) to give the title compound as a yellow solid. LRMS m/z (M+H) 293.1 found, 293.1 required.

Step 3: 4-(2,2-Difluoroethoxy)-2-fluoropyridine

To a solution of 2,2-difluoroethanol (200 mg, 2.44 mmol) in DMF (4.0 mL) was added sodium hydride (60% dispersion in mineral oil, 195 mg, 4.88 mmol) at 0° C. and the mixture was stirred at 0° C. for 0.5 h. A solution of 2,4-difluoropyridine (337 mg, 2.93 mmol) in DMF (0.5 ml) was added. The resulting mixture was warmed to RT and stirred for 2 h, then poured into water and extracted 3× with EtOAc. The combined organic layers were washed with brine, dried over magnesium sulfate, and concentrated in vacuo. The residue was purified by silica gel gradient chromatography (1:5 EtOAc in petroleum ether) to give the title compound as a colorless oil. LRMS m/z (M+H) 178.0 found, 178.0 required.

Step 4: (2-(2H-1,2,3-Triazol-2-yl)thiophen-3-yl)((2R,5R)-5-((4-(2,2-difluoroethoxy)pyridin-2-yl)oxy)-2-methylpiperidin-1-yl)methanone To a solution of (2-(2H-1,2,3-triazol-2-yl)thiophen-3-yl)((2R,5R)-5-hydroxy-2-methylpiperidin-1-yl)methanone (145 mg, 0.50 mmol) in DMF (5 mL) was added sodium hydride (60% dispersion in mineral oil, 40 mg, 1.0 mmol) at 0° C. The suspension was stirred for 0.5 h and 4-(2,2-difluoroethoxy)-2-fluoropyridine (105 mg, 0.60 mmol) was added. The reaction mixture was warmed to RT and stirred for 9 h, quenched with saturated, aqueous NH$_4$Cl, diluted with saturated, aqueous NaHCO$_3$, and extracted 2× with EtOAc. The organic layers were combined, washed with water and brine, dried over magnesium sulfate, filtered, and concentrated in vacuo. The residue was purified by silica gel gradient chromatography (1:2 EtOAc in petroleum ether) to give the title compound as a white solid. LRMS m/z (M+H) 450.1 found, 450.1 required.

TABLE 9

The following compound was prepared using the foregoing methodology and general procedure described in Example 60, but substituting the appropriate pyridine for 4-(2,2-difluoroethoxy)-2-fluoropyridine, as described in the foregoing Reaction Schemes and Examples. The requisite starting materials were commercially available, described in the literature or readily synthesized by one skilled in the art of organic synthesis from commerically available reagents using conventional reactions without undue experimentation.

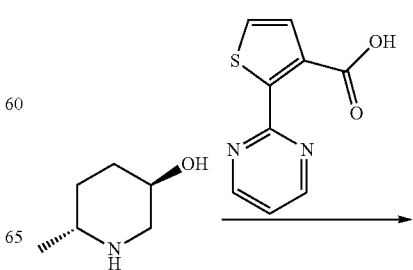

| Example | R | Name | LRMS (M + H⁺) |
|---|---|---|---|
| 61 | isopropyl | 4-(1-methylethoxy)-2-{[(3R,6R)-6-methyl-1-{[2-(2H-1,2,3-triazol-2-yl)thiophen-3-yl]carbonyl}piperidin-3-yl]oxy}pyridine | Calc'd 428.2, found 428.2 |
| 62 | ethyl | 4-ethoxy-2-{[(3R,6R)-6-methyl-1-{[2-(2H-1,2,3-triazol-2-yl)thiophen-3-yl]carbonyl}piperidin-3-yl]oxy}pyridine | Calc'd 414.2, found 414.1 |
| 63 | CF$_2$CF$_2$— | 2-{[(3R,6R)-6-methyl-1-{[2-(2H-1,2,3-triazol-2-yl)thiophen-3-yl]carbonyl}piperidin-3-yl]oxy}-4-(2,2,2-trifluoroethoxy)pyridine | Calc'd 468.1, found 468.1 |

EXAMPLE 64

-continued

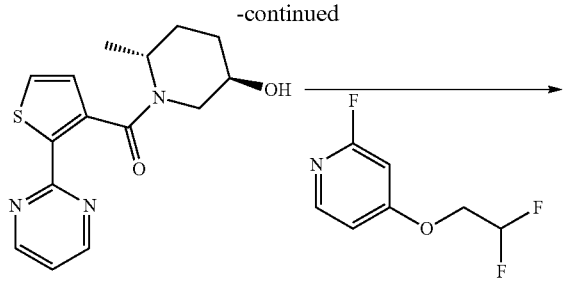

((2R,5R)-5-((4-(2,2-Difluoroethoxy)pyridin-2-yl)oxy)-2-methylpiperidin-1-yl)(2-(pyrimidin-2-yl)thiophen-3-yl)methanone Step 1: ((2R,5R)-5-Hydroxy-2-methylpiperidin-1-yl)(2-(pyrimidin-2-yl)thiophen-3-yl)methanone To a suspension of 2-(pyrimidin-2-yl)thiophene-3-carboxylic acid (300 mg, 1.46 mmol) in dichloromethane (15 mL) was added SOCl₂ (347 mg, 2.91 mmol). The mixture was heated at 40° C. for 2 h. After cooling to RT, the mixture was concentrated in vacuo and was added dropwise to a solution of (3R,6R)-6-methylpiperidin-3-ol hydrochloride (115 mg, 1.00 mmol) in dichloromethane (15 mL) at 0° C. Triethylamine (377 mg, 4.73 mmol) was added and the mixture was allowed to warm to RT and stirred overnight. The mixture was quenched with water and extracted 3× with dichloromethane. The combined organic layers were washed with brine, dried over magnesium sulfate, filtered, and concentrated in vacuo. The residue was purified by prep-TLC (1:1 EtOAc in petroleum ether), providing the title compound. LRMS m/z (M+H) 304.1 found, 304.1 required.

Step 2: (2-(2H-1,2,3-Triazol-2-yl)thiophen-3-yl)((2R,5R)-5-((4-(2,2-difluoroethoxy)pyridin-2-yl)oxy)-2-methylpiperidin-1-yl)methanone To a solution of ((2R,5R)-5-hydroxy-2-methylpiperidin-1-yl)(2-(pyrimidin-2-yl)thiophen-3-yl)methanone (50 mg, 0.17 mmol) in DMF (2.0 mL) was added sodium hydride (60% dispersion in mineral oil, 14 mg, 0.34 mmol) at 0° C. The suspension was stirred for 0.5 h and 4-(2,2-difluoroethoxy)-2-fluoropyridine (60 mg, 0.34 mmol) was added. The reaction mixture was allowed to warm to RT and stirred for 9 h. The mixture was quenched with saturated, aqueous NH₄Cl, diluted with saturated, aqueous NaHCO₃, and extracted 3× with EtOAc. The organic layers were combined, washed with water and brine, dried over magnesium sulfate, filtered, and concentrated in vacuo. The residue was purified by prep-HPLC to give the title compound as a white solid. LRMS m/z (M+H) 461.1 found, 461.1 required.

EXAMPLE 65

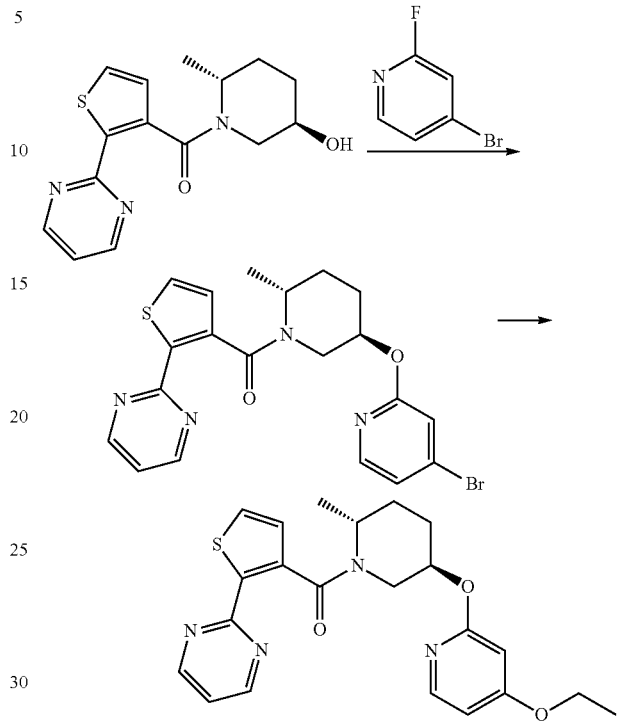

((2R,5R)-5-(4-Ethoxypyridin-2-yloxy)-2-methylpiperidin-1-yl)(2-(pyrimidin-2-yl)thiophen-3-yl)methanone Step 1: ((2R,5R)-5-(4-Bromopyridin-2-yloxy)-2-methylpiperidin-1-yl)(2-(pyrimidin-2-yl)thiophen-3-yl) methanone To a solution of ((2R,5R)-5-hydroxy-2-methylpiperidin-1-yl)(2-(pyrimidin-2-yl)thiophen-3-yl) methanone (100 mg, 0.33 mmol) in tetrahydrofuran (5 mL) was added sodium hydride (66 mg, 1.65 mmol) at 0° C. The mixture was stirred at 0° C. for 0.5 h, then 4-bromo-2-fluoropyridine (123 mg, 0.66 mmol) was added. The mixture was allowed to warm to RT and stirred for 2 h. The mixture was quenched with water and extracted 3× with dichloromethane. The combined organic layers were washed with brine, dried over magnesium sulfate, filtered, and concentrated in vacuo. The residue was purified by prep-TLC (1:1 EtOAc in petroleum ether), providing the title compound. LRMS m/z (M+H) 458.9 and 460.9 found, 459.0 and 461.0 required.

Step 2: ((2R,5R)-5-(4-Ethoxypyridin-2-yloxy)-2-methylpiperidin-1-yl)(2-(pyrimidin-2-yl)thiophen-3-yl)methanone A suspension of sodium (13 mg, 0.54 mmol) in ethanol (3 mL) was stirred at RT until the sodium was completely dissolved. ((2R,5R)-5-(4-Bromopyridin-2-yloxy)-2-methylpiperidin-1-yl)(2-(pyrimidin-2-yl)thiophen-3-yl) methanone (50 mg, 0.11 mmol) was added. The resulting mixture was heated at 80° C. overnight. After cooling to RT, the mixture was concentrated in vacuo. The residue was purified by prep-HPLC to give the title compound. LRMS m/z (M+H) 425.1 found, 425.1 required.

TABLE 10

The following compound was prepared using the foregoing methodology and general procedure described in Example 65. The requisite starting materials were commercially available, described in the literature or readily synthesized by one skilled in the art of organic synthesis from commerically available reagents using conventional reactions without undue experimentation.

| Example | R | Name | LRMS (M + H+) |
|---|---|---|---|
| 66 | | 2-(3-{[(2R,5R)-2-methyl-5-{[4-(2,2,2-trifluoroethoxy)pyridin-2-yl]oxy}piperidin-1-yl]carbonyl}thiophen-2-yl)pyrimidine | Calc'd 479.1, found 479.1 |

TABLE 11

The following table shows representative data for the compounds of the Examples as orexin receptor antagonists as determined by the assays described herein.

| Example | hOX2R FLIPR IC$_{50}$ (nM) | hOX1R FLIPR IC$_{50}$ (nM) |
|---|---|---|
| 1 | 20.5 | 859 |
| 2 | 12.5 | 617 |
| 3 | 14.7 | 843 |
| 4 | 59.4 | 1851 |
| 5 | 15.1 | 669 |
| 6 | 19 | 2177 |
| 7 | 23 | 1198 |
| 8 | 35.4 | 2008 |
| 10 | 14.7 | 576 |
| 12 | 11.0 | 938 |
| 13 | 56.2 | 1755 |
| 14 | 34.8 | 1981 |
| 15 | 24.5 | 746 |
| 17 | 27 | 1605 |
| 18 | 94.5 | 10000 |
| 19 | 22.1 | 1800 |
| 20 | 114 | 10000 |
| 21 | 38.3 | 8194 |
| 23 | 41.2 | 2145 |
| 24 | 136 | 10000 |
| 25 | 110 | 10000 |
| 26 | 37.2 | 2479 |
| 27 | 12 | 1418 |
| 28 | 8 | 1345 |
| 29 | 29 | 8074 |
| 30 | 38 | 10000 |
| 31 | 34 | >10,000 |
| 32 | 24 | 4355 |
| 33 | 71 | >10,000 |
| 34 | 42 | 2142 |
| 35 | 62 | 3269 |

TABLE 11-continued

The following table shows representative data for the compounds of the Examples as orexin receptor antagonists as determined by the assays described herein.

| Example | hOX2R FLIPR IC$_{50}$ (nM) | hOX1R FLIPR IC$_{50}$ (nM) |
|---|---|---|
| 36 | 56 | 2973 |
| 37 | 52 | 2722 |
| 38 | 56 | 2502 |
| 40 | 15.2 | 581 |
| 42 | 134 | 5611 |
| 43 | 38.7 | 2490 |
| 44 | 67.0 | 1637 |
| 45 | 33 | 2944 |
| 46 | 63 | 3522 |
| 47 | 84 | 9272 |
| 48 | 9.7 | 568 |
| 49 | 71 | 10,000 |
| 50 | 37.5 | 6747 |
| 51 | 12.3 | 976 |
| 52 | 4 | 194 |
| 53 | 8 | 490 |
| 54 | 11 | 1018 |
| 55 | 13 | 1760 |
| 56 | 11 | 1145 |
| 57 | 11 | 1690 |
| 58 | 21 | 1107 |
| 59 | 11 | 1264 |
| 60 | 22 | 2017 |
| 61 | 25 | 1479 |
| 62 | 22 | 1162 |
| 63 | 55 | 8381 |
| 64 | 36 | 5214 |
| 65 | 26 | 899 |
| 66 | 26 | 2080 |

With respect to other piperidine compounds such as those disclosed in WO 2010/048012, it would be desirable that the present compounds exhibit unexpected properties, such as increased selectivity at the orexin-2 receptor relative to the orexin-1 receptor. For example, relative to 2-pyridyloxy compounds of WO2010/048012 that do not possess a 2-pyridyloxy-4-ether substituent, the compounds of the examples possess greater selectivity for the orexin-2 receptor than for the orexin-1 receptor.

For example, the following 2-pyridyloxy compounds are disclosed in WO 2010/048012:

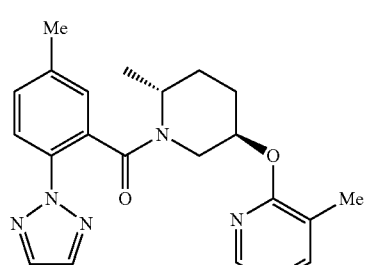

Example 1-3 hOX2R IC$_{50}$ = 32 nM
hOX1R IC$_{50}$ = 375 nM
Selectivity 12x

Example 1-4

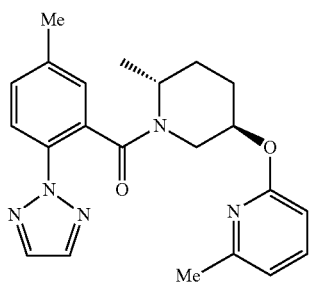

hOX2R IC$_{50}$ = 47 nM
hOX1R IC$_{50}$ = 180 nM
Selectivity 3.8x

Representative compounds herein are the compounds of Example 1, 6, 12, 19, 27, 28, 31, 32, 54 and 59.

Example 1

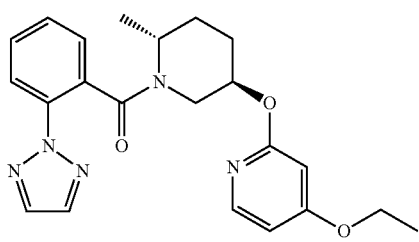

hOX2R IC$_{50}$ = 20 nM
hOX1R IC$_{50}$ = 888 nM
Selectivity 44x

Example 6

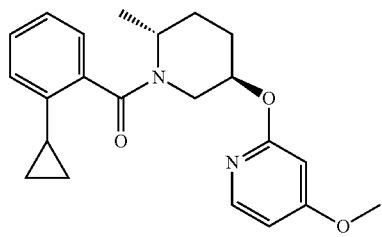

hOX2R IC$_{50}$ = 19 nM
hOX1R IC$_{50}$ = 2177 nM
Selectivity 115x

Example 12 hOX2R IC$_{50}$ = 11 nM
hOX1R IC$_{50}$ = 938 nM
Selectivity 85x

Example 19

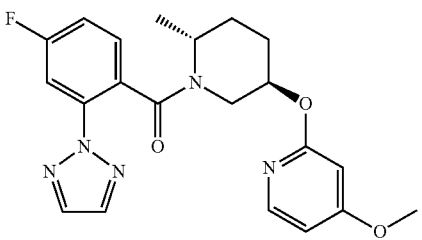

hOX2R IC$_{50}$ = 22.1 nM
hOX1R IC$_{50}$ = 1800 nM
Selectivity 81x

Example 27 hOX2R IC$_{50}$ = 12 nM
hOX1R IC$_{50}$ = 1418 nM
Selectivity 118x

Example 28

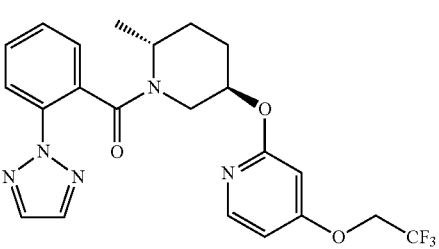

hOX2R IC$_{50}$ = 8 nM
hOX1R IC$_{50}$ = 1345 nM
Selectivity 168x

Example 31

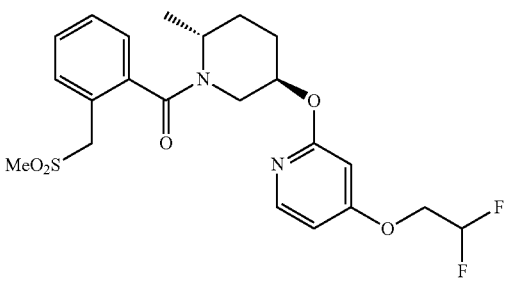

hOX2R IC$_{50}$ = 34 nM
hOX1R IC$_{50}$ = >10,000 nM
Selectivity >294x

-continued

Example 32

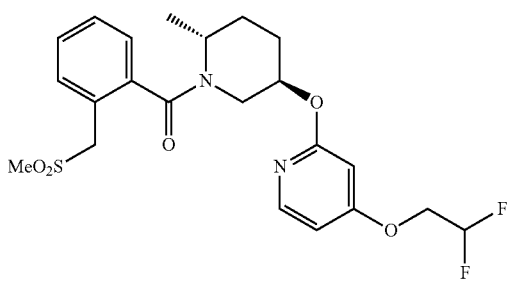

hOX2R IC$_{50}$ = 34 nM
hOX1R IC$_{50}$ = >10,000 nM
Selectivity >294x

Example 54

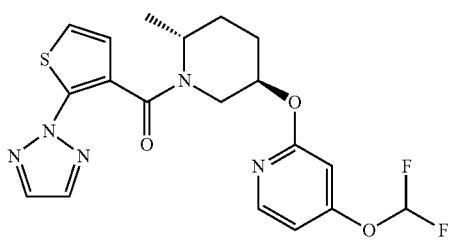

hOX2R IC$_{50}$ = 11 nM
hOX1R IC$_{50}$ = 1018 nM
Selectivity 92.5x

Example 59

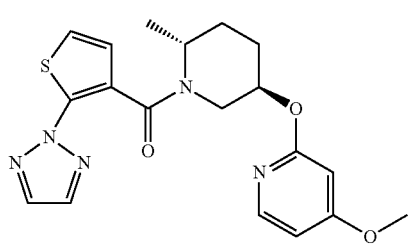

hOX2R IC$_{50}$ = 11 nM
hOX1R IC$_{50}$ = 1264 nM
Selectivity 115x

As indicated by the data herein, the compounds of the present examples provide greater functional selectivity for the orexin-2 receptor over the orexin-1 receptor. The distinction in potency between the orexin-2 receptor and the orexin-1 receptor in the whole cell FLIPR functional assay provides enhanced predictive value for determining in vivo efficacy. Increasing the functional selectivity for the orexin-2 receptor reduces the potential for dual receptor antagonism in vivo. Such greater functional selectivity may provide benefits over other orexin receptor antagonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula Ia:

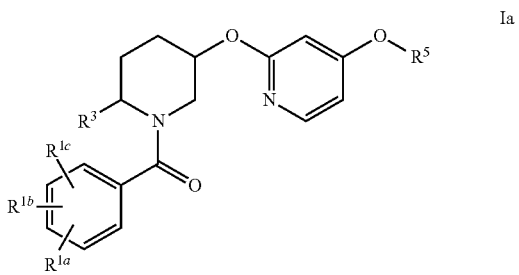

wherein:
$R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) —CN, and
(7) 1,2,3-triazolyl, which is unsubstituted or substituted with halogen, hydroxyl, $C_{1-6}$alkyl, —O—$C_{1-6}$alkyl or —NO$_2$, wherein only one of $R^{1a}$, $R^{1b}$ and $R^{1c}$ may be 1,2,3-triazolyl;
$R^3$ is methyl;
$R^5$ is selected from the group consisting of:
(1) $C_{1-6}$alkyl, which is unsubstituted or substituted with halogen or phenyl,
(2) $C_{3-6}$cycloalkyl, which is unsubstituted or substituted with $C_{1-6}$alkyl, halogen or phenyl, and
(3) phenyl, which is unsubstituted or substituted with $C_{1-6}$alkyl, halogen or phenyl;
or a pharmaceutically acceptable salt thereof.

2. The compound of claim 1 or a pharmaceutically acceptable salt thereof wherein $R^5$ is selected from the group consisting of:
(1) $C_{1-6}$alkyl, which is unsubstituted or substituted with halogen or phenyl,
(2) $C_{3-6}$cycloalkyl, which is unsubstituted or substituted with $C_{1-6}$alkyl or halogen, and
(3) phenyl.

3. The compound of claim 1 or a pharmaceutically acceptable salt thereof wherein $R^5$ is selected from the group consisting of: methyl, fluoro-methyl, difluoro-methyl, ethyl, fluoroethyl, isopropyl, cyclopropyl, butyl, 2,2-difluoro-ethyl, phenyl, and benzyl.

4. The compound of claim 1 or a pharmaceutically acceptable salt thereof wherein $R^5$ is methyl, ethyl or isopropyl.

5. A compound which is selected from the group consisting of:
4-ethoxy-2-{[(3R,6R)-6-methyl-1-{[2-(2H-1,2,3-triazol-2-yl)phenyl]carbonyl}piperidin-3-yl]oxy}pyridine;
4-methoxy-2-{[(3R,6R)-6-methyl-1-{[2-(2H-1,2,3-triazol-2-yl)phenyl]carbonyl}piperidin-3-yl]oxy}pyridine;
3-bromo-4-methoxy-2-{[(3R,6R)-6-methyl-1-{[2-(2H-1,2,3-triazol-2-yl)phenyl]carbonyl}piperidin-3-yl]oxy}pyridine;
4-(benzyloxy)-2-{[(3R,6R)-6-methyl-1-{[2-(2H-1,2,3-triazol-2-yl)phenyl]carbonyl}piperidin-3-yl]oxy}pyridine;

4-(1-methylethoxy)-2-{[(3R,6R)-6-methyl-1-{[2-(2H-1,2,3-triazol-2-yl)phenyl]carbonyl}piperidin-3-yl]oxy}pyridine;

4-methoxy-2-{[(3R,6R)-6-methyl-1-{[4-(2H-1,2,3-triazol-2-yl)pyridin-3-yl]carbonyl}piperidin-3-yl]oxy}pyridine;

2-{[(3R,6R)-1-{[3-fluoro-2-(2H-1,2,3-triazol-2-yl)phenyl]carbonyl}-6-methylpiperidin-3-yl]oxy}-4-methoxypyridine;

3-({(2R,5R)-5-[(4-methoxypyridin-2-yl)oxy]-2-methylpiperidin-1-yl}carbonyl)-4-(2H-1,2,3-triazol-2-yl)benzamide;

2-({(3R,6R)-1-[(2-cyclopropylphenyl)carbonyl]-6-methylpiperidin-3-yl}oxy)-4-methoxypyridine;

4-methoxy-2-{[(3R,6R)-6-methyl-1-{[2-(trifluoromethyl)phenyl]carbonyl}piperidin-3-yl]oxy}pyridine;

2-({(3R,6R)-1-[(2-ethoxyphenyl)carbonyl]-6-methylpiperidin-3-yl}oxy)-4-methoxypyridine;

6-methoxy-3-({(2R,5R)-5-[(4-methoxypyridin-2-yl)oxy]-2-methylpiperidin-1-yl}carbonyl)-2-phenylpyridine;

2-{[(3R,6R)-1-{[2-fluoro-6-(2H-1,2,3-triazol-2-yl)phenyl]carbonyl}-6-methylpiperidin-3-yl]oxy}-4-methoxypyridine;

6-methoxy-3-({(2R,5R)-5-[(4-methoxypyridin-2-yl)oxy]-2-methylpiperidin-1-yl}carbonyl)-2-(2H-1,2,3-triazol-2-yl)pyridine;

2-{[(3R,6R)-1-{[4-fluoro-2-(2H-1,2,3-triazol-2-yl)phenyl]carbonyl}-6-methylpiperidin-3-yl]oxy}-4-methoxypyridine;

4-methoxy-2-{[(3R,6R)-1-{[4-methoxy-2-(2H-1,2,3-triazol-2-yl)phenyl]carbonyl}-6-methylpiperidin-3-yl]oxy}pyridine;

2-cyclopropyl-6-methoxy-3-({(2R,5R)-5-[(4-methoxypyridin-2-yl)oxy]-2-methylpiperidin-1-yl}carbonyl)pyridine;

2-chloro-6-methoxy-3-({(2R,5R)-5-[(4-methoxypyridin-2-yl)oxy]-2-methylpiperidin-1-yl}carbonyl)pyridine;

2-{[(3R,6R)-1-{[4-fluoro-2-(2H-1,2,3-triazol-2-yl)phenyl]carbonyl}-6-methylpiperidin-3-yl]oxy}-4-(1-methylethoxy)pyridine;

2-{[(3R,6R)-1-{[4-methoxy-2-(2H-1,2,3-triazol-2-yl)phenyl]carbonyl}-6-methylpiperidin-3-yl]oxy}-4-(1-methyl ethoxy)pyridine;

6-methoxy-3-{[(2R,5R)-2-methyl-5-{[4-(1-methylethoxy)pyridin-2-yl]oxy}piperidin-1-yl]carbonyl}-2-(2H-1,2,3-triazol-2-yl)pyridine;

2-{[(3R,6R)-1-{[5-fluoro-2-(2H-1,2,3-triazol-2-yl)phenyl]carbonyl}-6-methylpiperidin-3-yl]oxy}-4-(1-methylethoxy)pyridine;

(2-(2H-1,2,3-triazol-2-yl)phenyl)((2R,5R)-5-((4-(2,2-difluoroethoxy)pyridin-2-yl)oxy)-2-methylpiperidin-1-yl)methanone;

(2-(2H-1,2,3-triazol-2-yl)phenyl)((2R,5R)-2-methyl-5-((4-(2,2,2-trifluoroethoxy)pyridin-2-yl)oxy)piperidin-1-yl)methanone;

4-(2,2-difluoroethoxy)-2-{[(3R,6R)-6-methyl-1-({2-[(methylsulfonyl)methyl]phenyl}carbonyl)-piperidin-3-yl]oxy}pyridine;

1-(2-{[(2R,5R)-5-{[4-(2,2-difluoroethoxy)pyridin-2-yl]oxy}-2-methylpiperidin-1-yl]carbonyl}phenyl)cyclopropanecarbonitrile;

2-{[(2R,5R)-5-{[4-(2,2-difluoroethoxy)pyridin-2-yl]oxy}-2-methylpiperidin-1-yl]carbonyl}-3-(2H-1,2,3-triazol-2-yl)pyridine;

4-(2,2-difluoroethoxy)-2-{[(3R,6R)-1-{[3-fluoro-2-(2H-1,2,3-triazol-2-yl)phenyl]carbonyl}-6-methylpiperidin-3-yl]oxy}pyridine;

4-(2,2-difluoroethoxy)-2-{[(3R,6R)-1-{[4-fluoro-2-(2H-1,2,3-triazol-2-yl)phenyl]carbonyl}-6-methylpiperidin-3-yl]oxy}pyridine;

4-(2,2-difluoroethoxy)-2-{[(3R,6R)-1-{[2-fluoro-6-(2H-1,2,3-triazol-2-yl)phenyl]carbonyl}-6-methylpiperidin-3-yl]oxy}pyridine;

4-(cyclopropyloxy)-2-{[(3R,6R)-6-methyl-1-{[2-(2H-1,2,3-triazol-2-yl)phenyl]carbonyl}-piperidin-3-yl]oxy}pyridine;

2-{[(3R,6R)-6-methyl-1-{[2-(2H-1,2,3-triazol-2-yl)phenyl]carbonyl}piperidin-3-yl]oxy}-4-(oxetan-3-yloxy)pyridine;

4-(2-methylpropoxy)-2-{[(3R,6R)-6-methyl-1-{[2-(2H-1,2,3-triazol-2-yl)phenyl]carbonyl}piperidin-3-yl]oxy}pyridine;

2-{[(3R,6R)-6-methyl-1-{[2-(2H-1,2,3-triazol-2-yl)phenyl]carbonyl}piperidin-3-yl]oxy}-4-propoxypyridine;

1-(4-methoxy-2-{[(3R,6R)-6-methyl-1-{[2-(2H-1,2,3-triazol-2-yl)phenyl]carbonyl}piperidin-3-yl]oxy}pyridin-3-yl)ethanone;

(2-(2H-1,2,3-triazol-2-yl)phenyl)((2R,5R)-5-((4-(difluoromethoxy)pyridin-2-yl)oxy)-2-methylpiperidin-1-yl)methanone;

(2-(2H-1,2,3-triazol-2-yl)phenyl)((2R,5R)-5-((4-(fluoromethoxy)pyridin-2-yl)oxy)-2-methylpiperidin-1-yl)methanone; and 1-(2-{[(2R,5R)-5-{[4-(difluoromethoxy)pyridin-2-yl]oxy}-2-methylpiperidin-1-yl]carbonyl}-phenyl)cyclopropanecarbonitrile;

or a pharmaceutically acceptable salt thereof.

6. A pharmaceutical composition which comprises an inert carrier and a compound of claim 1 or a pharmaceutically acceptable salt thereof.

* * * * *